(12) United States Patent
Arita et al.

(10) Patent No.: US 9,889,032 B2
(45) Date of Patent: Feb. 13, 2018

(54) DIGESTIVE TRACT DEVICE

(71) Applicant: TERUMO KABUSHIKI KAISHA, Shibuya-ku, Tokyo (JP)

(72) Inventors: Eiji Arita, Hadano (JP); Naoki Aramaki, Atsugi (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 106 days.

(21) Appl. No.: 14/869,474

(22) Filed: Sep. 29, 2015

(65) Prior Publication Data
US 2016/0022463 A1    Jan. 28, 2016

Related U.S. Application Data

(63) Continuation of application No. PCT/JP2013/060016, filed on Apr. 1, 2013.

(51) Int. Cl.
*A61M 5/00* (2006.01)
*A61F 5/00* (2006.01)
*A61B 17/11* (2006.01)

(52) U.S. Cl.
CPC ........ *A61F 5/0089* (2013.01); *A61B 17/1114* (2013.01); *A61F 5/0076* (2013.01); *A61B 2017/1132* (2013.01)

(58) Field of Classification Search
CPC ............................. A61F 5/0076; A61F 5/0089
See application file for complete search history.

(56) References Cited

U.S. PATENT DOCUMENTS

| | | | |
|---|---|---|---|
| 7,803,195 B2 | 9/2010 | Levy et al. | |
| 2005/0273060 A1 | 12/2005 | Levy et al. | |
| 2006/0009858 A1 * | 1/2006 | Levine | A61F 2/04 623/23.65 |
| 2008/0255678 A1 | 10/2008 | Cully et al. | |
| 2010/0305590 A1 | 12/2010 | Holmes et al. | |
| 2011/0172584 A1 | 7/2011 | Chin | |
| 2012/0179086 A1 * | 7/2012 | Shank | A61F 2/04 604/8 |
| 2013/0165841 A1 * | 6/2013 | Priplata | A61F 5/00 604/8 |

FOREIGN PATENT DOCUMENTS

| | | |
|---|---|---|
| JP | 2011-517599 A | 6/2011 |
| WO | WO 2008/127552 A2 | 10/2008 |
| WO | WO 2009/126294 A1 | 10/2009 |
| WO | WO 2011/088381 A1 | 7/2011 |

OTHER PUBLICATIONS

International Search Report (PCT/ISA/210) dated Jul. 9, 2013, by the Japanese Patent Office as the International Searching Authority for International Application No. PCT/JP2013/060016.

* cited by examiner

*Primary Examiner* — Leslie Deak
(74) *Attorney, Agent, or Firm* — Buchanan Ingersoll & Rooney PC

(57) ABSTRACT

A digestive tract device that can reduce an indwelling-induced burden on the living body includes: a tubular portion that includes a through hole; a holding portion that is provided on a proximal end side of the tubular portion, and holds the tubular portion in the living body; and support portions and which are provided in the holding portion, and are in contact with a plurality of sites of the digestive organ of the living body, and support the holding portion in such a way that the holding portion can move in at least one direction of a circumferential direction and a longitudinal direction of the tubular portion.

20 Claims, 25 Drawing Sheets

DIGESTIVE TRACT DEVICE

CROSS-REFERENCES TO RELATED APPLICATIONS

This application is a continuation of International Application No. PCT/JP2013/060016 filed on Apr. 1, 2013, the entire content of which is incorporated herein by reference.

TECHNICAL FIELD

The present invention generally relates to a digestive tract device that is placed inside the digestive tract.

BACKGROUND DISCUSSION

In recent years, a bypass surgery by which the upper part of the stomach is directly connected to the lower part of the small intestine in a surgical manner has been deemed to be effective in treating diabetes (especially type 2 diabetes) and obesity. In a state where such a bypass surgery is performed, since the ingested nutrients directly flow into the lower part of the small intestine from the upper part of the stomach, nutrients do not flow to the duodenum and the upper part of the jejunum which are the upper parts of the small intestine. As a result, it is possible to reduce the absorption of nutrients. Since nutrients do not flow to the upper part of the small intestine, glucose-dependent insulinotropic polypeptide (GIP), glucagon, and the like that are gastrointestinal hormones which are secreted due to a stimulus by nutrients are less likely to be secreted. In addition, when undigested nutrients pass through the lower part of the jejunum and the ileum which are the lower parts of the small intestine, glucagon-like peptide-1 (GLP-1) which is a gastrointestinal hormone is increasingly secreted due to stimulus by nutrients. GIP and glucagon are deemed to be factors which reduce the amount of secretion of insulin, and since GIP and glucagon are not secreted, the secretion of insulin is less likely to be inhibited. In addition, GLP-1 is deemed to be a factor which stimulates the secretion of insulin. As described above, the absorption of ingested nutrients is not only restricted, but the secretion of insulin is also stimulated due to the action of gastrointestinal hormones, and the blood glucose level is reduced, and thus the bypass surgery is deemed to be effective in the treatment of diabetes and obesity.

However, the bypass surgery is highly invasive, and thus in recent years, health professionals have given attention to a low-invasive method by which a sleeve allowing the flow of nutrients therethrough is placed on the upper part of the small intestine. For example, U.S. Pat. No. 7,803,1951 discloses a device including two balloons which are disposed with the pyloric ring of the stomach interposed between the two balloons, and a tubular sleeve which extends from the balloons toward the small intestine. U.S. Patent Application Publication No. US2010/0305590 discloses a device in which a projected anchor which is hooked onto the pyloric ring of the stomach is adopted instead of the balloons.

SUMMARY

When the device disclosed in U.S. Pat. No. 7,803,195 is used and indwelled on the pyloric ring, the balloons are in press contact with a wide circumferential range of the pyloric ring during indwelling. When external force such as contractile force induced by peristalsis of the digestive organs or tensile force occurring when fluids such as foods, or the like flow in the sleeve is applied to the device, the external force is transmitted to the pyloric ring via the balloons. Since the external force is repeatedly applied to the pyloric ring while the digestive tract device is indwelled, a heavy burden is imposed on the living body.

In contrast, when the device disclosed in U.S. Patent Application Publication No. US2010/0305590 is used, the device is indwelled in a state where the anchor bites into the pyloric ring, and thus a much heavier burden is imposed on the living body compared to when the device disclosed in U.S. Pat. No. 7,803,195 is used.

As described above, when the digestive tract devices in the related art are used, it is possible to realize a low invasive technique compared to a bypass surgery; however, a heavy burden is imposed on the living body during indwelling, and thus a task is to reduce the burden.

The digestive tract device disclosed here can reduce indwelling-induced burden on the living body.

A digestive tract device includes: a tubular portion that includes a through hole; a holding portion on a proximal end side of the tubular portion, with the holding portion being configured to hold the tubular portion in the living body; and support portions provided in the holding portion. The support portions are configured to contact a plurality of sites of the digestive organ of the living body while supporting the holding portion in such a way that the holding portion can move in at least one of a circumferential direction of the tubular portion and a longitudinal direction of the tubular portion.

The holding portion is formed from a shaped wire-like body, and the holding portion is formed by a hourglass-shaped neck portion of the wire-like body in such a way that the neck portion is in contact with the digestive organ.

The holding portion includes a twisted portion that is formed by twisting the wire-like body around an axis along the longitudinal direction of the tubular portion.

The holding portion includes a curved portion that is formed by bending the wire-like body in a direction intersecting an axis along the longitudinal direction of the tubular portion.

The holding portion has a movable blade that causes the holding portion to be able to move when an external force is applied to the movable blade.

The digestive tract device further includes: an engaging portion through which the holding portion is engaged with the tubular portion in such a way that the holding portion can rotate relative to the tubular portion.

The engaging portion includes an annular member that is attached to the tubular portion, and the holding portion includes an engaging portion that is hooked onto and is engaged with the annular member.

The engaging portion includes a tubular portion-side annular member which is attached to the tubular portion, and a holding portion-side annular member which is attached to the holding portion and engaged with the tubular portion-side annular member in such a way as to be able to rotate relative to the tubular portion-side annular member.

By virtue of the digestive tract device disclosed here, while in contact with a plurality of sites of the digestive organ of the living body, the holding portion is supported in such a way that the holding portion holding the tubular portion (into which fluids such as foods or the like flow) relative to the living body can move in the circumferential direction and the longitudinal direction of the tubular portion. For this reason, the position of contact between the holding portion and the digestive organ is appropriately changed while the tubular portion is held by the holding portion, and thus a contractile force induced by peristalsis, a pulling force induced by the inflow of fluids, or the like can be prevented from being locally applied to a specific site of the digestive organ over time, and an indwelling-induced burden on the living body can be suitably reduced.

Since the holding portion is formed from a wire-like body, it is possible to reduce the area of contact between the holding portion and the digestive organ, and to further reduce an indwelling-induced burden on the living body. Since the support portions are formed from portions of the wire-like body, it is possible to reduce the number of components, and it is possible to reduce manufacturing costs, or to simplify manufacturing operations.

The holding portion is caused to be able to move in the circumferential direction of the tubular portion by the twisted portion of the holding portion even if a smaller force is applied. For this reason, a burden can be suitably prevented from being locally applied to a specific site of the digestive organ.

The holding portion is able to move in the longitudinal direction of the tubular portion by the curved portion of the holding portion even if a smaller force is applied. For this reason, a burden can be suitably prevented from being locally applied to a specific site of the digestive organ.

The holding portion is able to move by the movable blade of the holding portion, and so a burden can be suitably prevented from being locally applied to a specific site of the digestive organ while the digestive tract device is indwelled.

Since the holding portion is engaged with the tubular portion in such a way as to be able to rotate relative to the tubular portion, when the holding portion rotates, the rotation of the holding portion can be prevented from being transmitted to the tubular portion, which in turn prevents the tubular portion from being twisted and kinked. For this reason, even if the holding portion repeatedly moves, fluids can smoothly flow downwards in the tubular portion.

Since the holding portion and the tubular portion are engaged with each other via the annular member attached to the tubular portion and the engaging portion of the holding portion in such a way as to be able to rotate relative to each other, it is possible to suitably prevent the rotation of the holding portion from causing the tubular portion to be twisted or kinked.

Because the holding portion and the tubular portion are engaged with each other via the tubular portion-side annular member attached to the tubular portion and the holding portion-side annular member attached to the holding portion in such a way as to be able to rotate relative to each other, it is possible to suitably prevent the rotation of the holding portion from causing the tubular portion to be twisted or kinked.

According to another aspect, a method comprises: introducing a tubular portion and a holding portion into a digestive tract of a living body, wherein the tubular portion possesses a length and includes a through hole extending throughout the length of the tubular portion, and the holding portion holds the tubular portion on a proximal end of the tubular portion; and positioning the tubular portion and the holding portion in the digestive tract so that at least a part of the tubular portion is on a distal side of a site in the digestive tract of the living body. The site possesses an inner diameter smaller than an inner diameter of a portion of the digestive tract immediately proximal of the site and smaller than an inner diameter of a portion of the digestive tract immediately distal of the site. The method further involves supporting the tubular portion in the digestive tract through contact of the holding portion with the digestive tract at a plurality of spaced apart locations on a proximal side of the site. The holding portion in contact with the digestive tract is movable, relative to the tubular portion, in at least one of a circumferential direction of the tubular portion and a longitudinal direction of the tubular portion.

DETAILED DESCRIPTION

Figure 1:
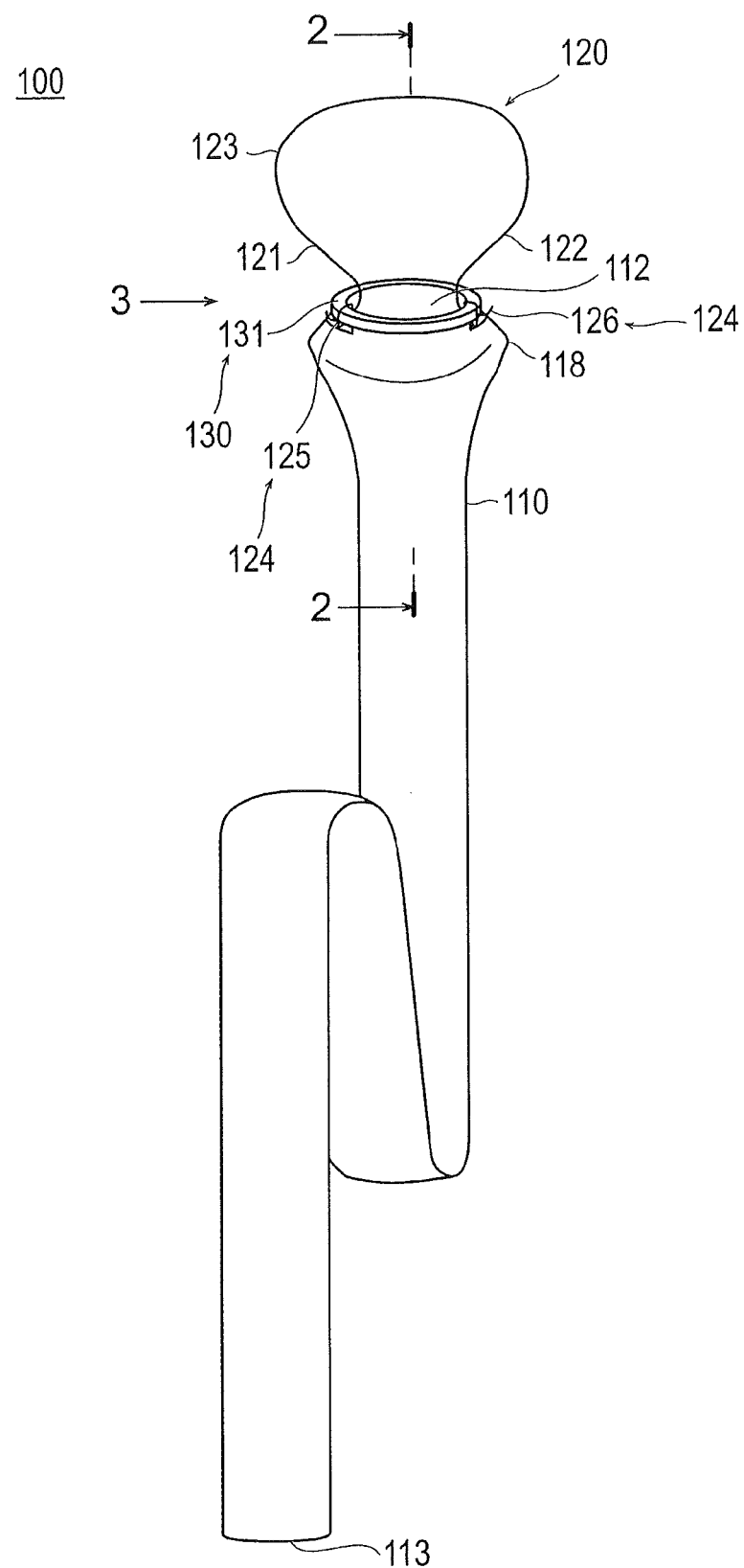
FIG. 1 is a schematic view of a digestive tract device according to a first embodiment disclosed here.

Hereinafter, embodiments of the digestive tract device representing examples of the inventive digestive tract device disclosed here will be described with reference to the accompanying drawings. For illustrative purposes, the drawings, inclusive of features shown in the drawings, may be overdrawn (i.e., may be enlarged), and dimensional ratios may be different from actual dimensional ratios.

Figure 2:
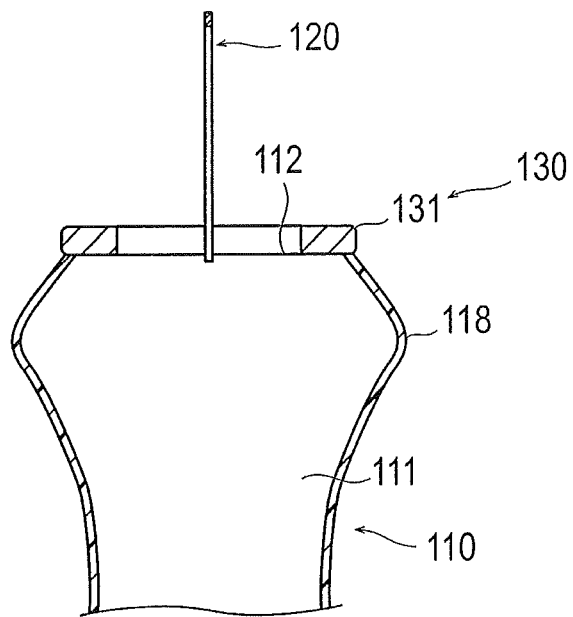
FIG. 2 is a cross-sectional view taken along the section line II-II in FIG. 1.
Figure 3:
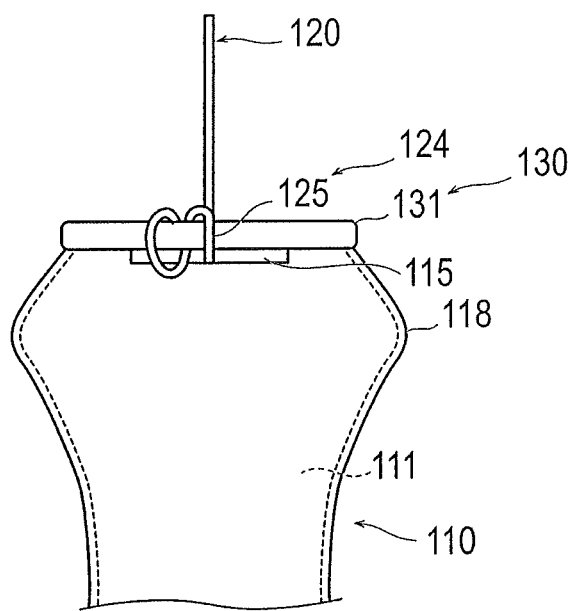
FIG. 3 is an enlarged view taken in a direction of arrow 3 in FIG. 1.
Figure 4:
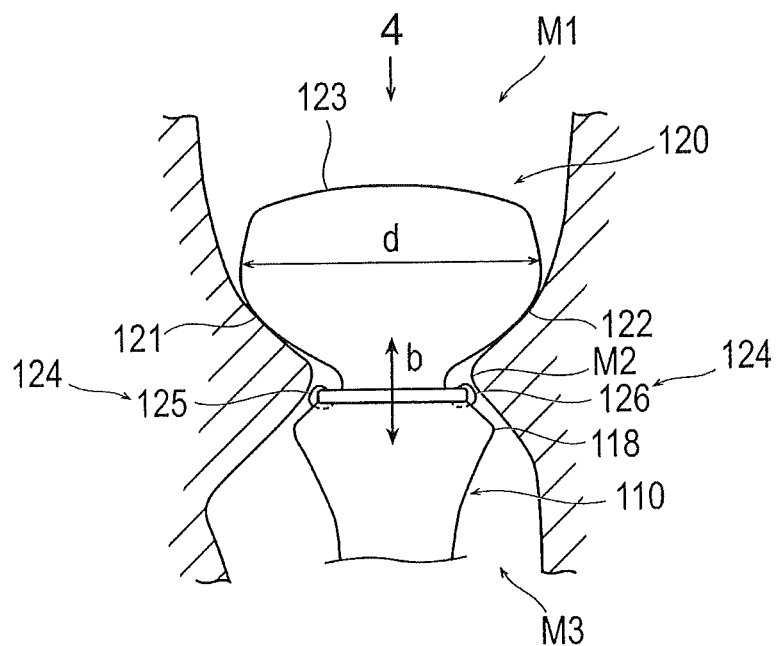
FIG. 4 is a cross-sectional view schematically illustrating a state in which the digestive tract device in the first embodiment is indwelled inside the living body.
Figure 5:
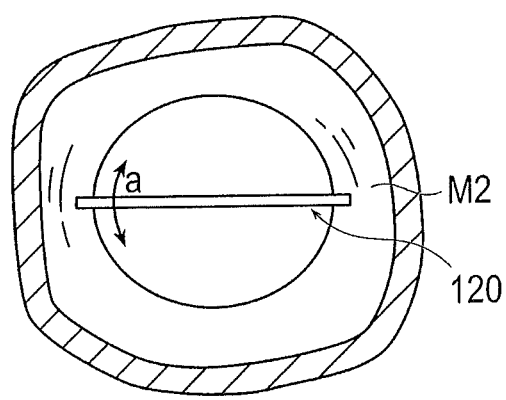
FIG. 5 is a cross-sectional view taken in a direction of arrow 4 in FIG. 4.
Figure 10:
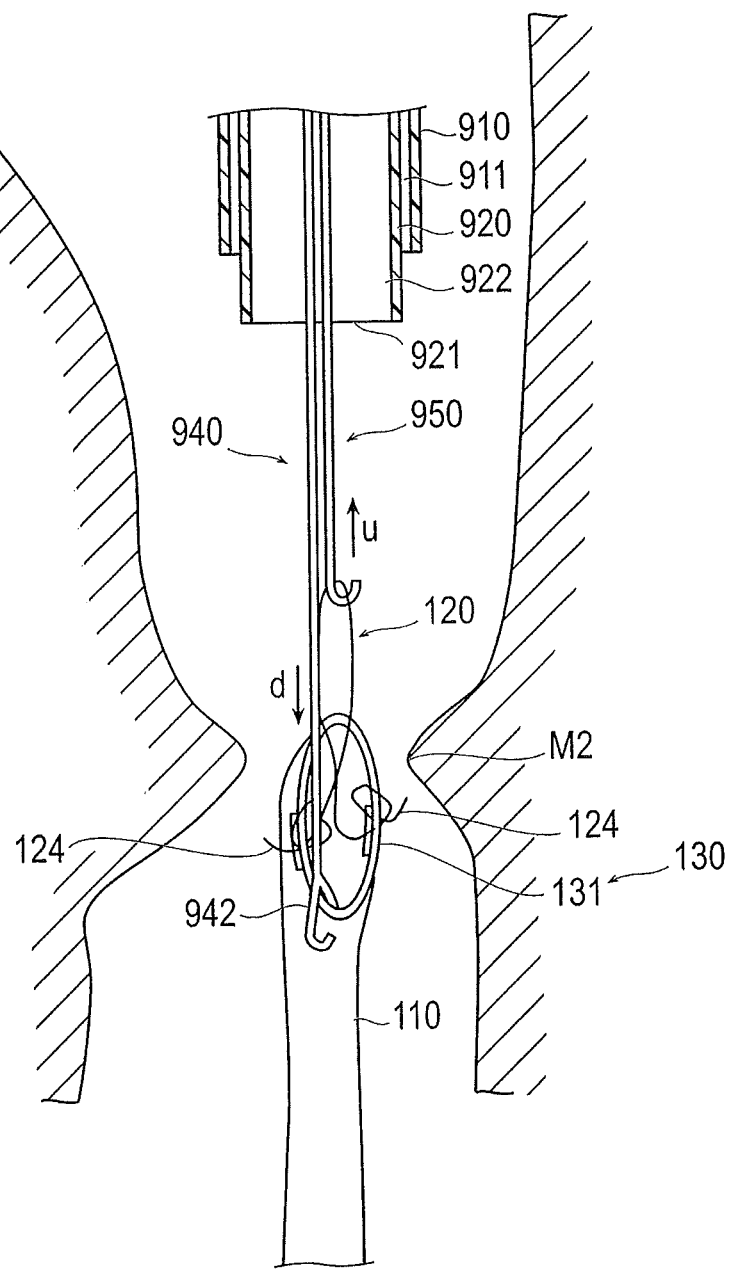
FIG. 10 is a cross-sectional view illustrating the sequence of removing the digestive tract device in the first embodiment from the living body.
Figure 11:
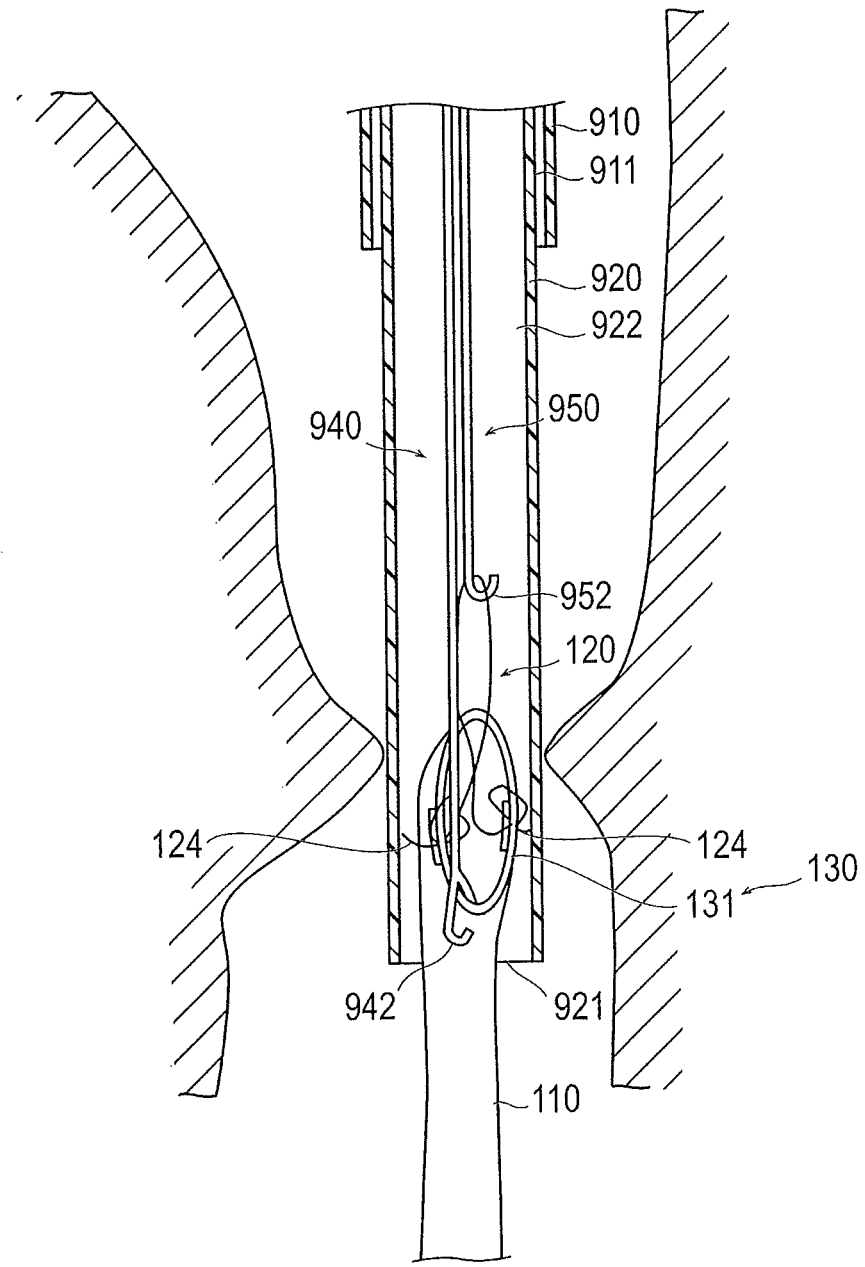
FIG. 11 is a cross-sectional view illustrating the sequence of removing the digestive tract device in the first embodiment from the living body.
Figure 12:
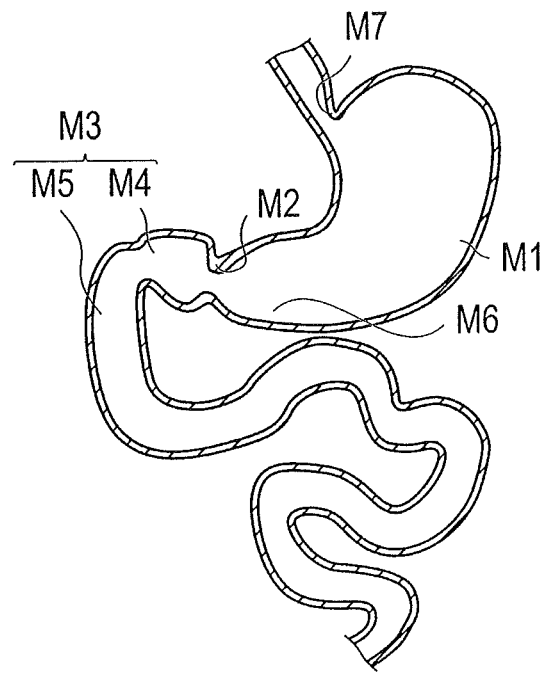
FIG. 12 is a cross-sectional view schematically illustrating the digestive organs of the living body.
Figure 13:
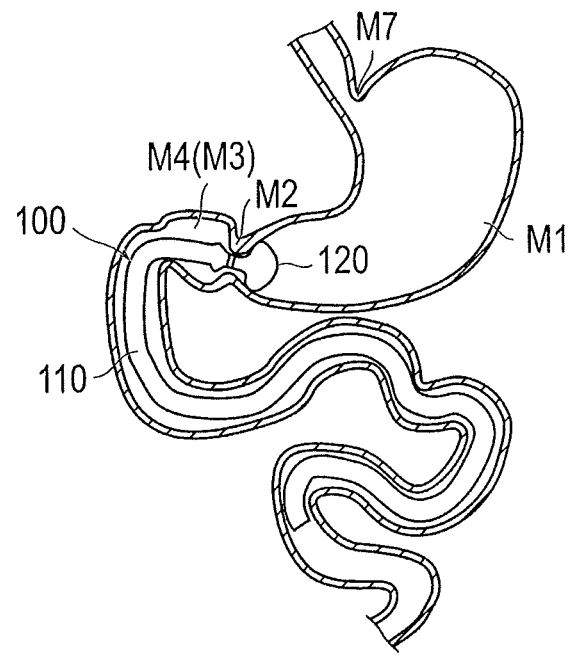
FIG. 13 is a cross-sectional view schematically illustrating a state in which the digestive tract device is indwelled inside the digestive organs of the living body.

FIGS. 1 to 3 illustrate the configuration of a digestive tract device according to one embodiment representing an example of the disclosed inventive digestive tract device, FIGS. 4 and 5 depict an operation of the digestive tract device, FIGS. 6 to 11 illustrate the method of indwelling and removing the digestive tract device, FIG. 12 depicts digestive organs of the living body that is a target object for the digestive tract device, and FIG. 13 shows a state in which the digestive tract device is indwelled inside the digestive organs of the living body.

As illustrated in FIGS. 1 to 3, generally speaking, a digestive tract device 100 in the embodiment includes a tubular portion 110 with a through hole 111, and a holding portion 120 that is provided on the proximal end side of the tubular portion 110, and holds the tubular portion 110 in the living body. As illustrated in FIGS. 4 and 5, the holding portion 120 is provided with support portions 121 and 122 which support the holding portion 120 while contacting a plurality of sites of the digestive organ of the living body in such a way that the holding portion 120 can move in at least one direction from amongst a circumferential direction and a longitudinal direction of the tubular portion 110.

In the following description of the digestive tract device 100, a distal end side or distal end refers to the side or end on which the tubular portion 110 is provided, and a proximal end side or proximal end refers to the side or end on which the holding portion 120 is provided. In the digestive tract, a distal side refers to the side on which the anus is present, and a proximal side refers to the side on which the mouth is present. The circumferential direction of the tubular portion 110 is a direction around the central axis of the tubular portion 110, and is represented by the arrow a in FIG. 5. The longitudinal direction of the tubular portion 110 is a direction that extends from the proximal end side of the tubular portion 110 toward the distal end side of the tubular portion 110, and is represented by arrow b in FIG. 4.

As illustrated in FIGS. 1 and 4, the holding portion 120 of the digestive tract device 100 can be formed from a shaped wire (wire-shaped)body. The support portions 121 and 122 of the holding portion 120 can be formed by a hourglass-shaped neck portion of the wire-shaped body (which forms the holding portion 120) in such a way that the neck portion is in contact with a pyloric ring M2 of the digestive organs.

In each of the embodiments to be described in this specification, the pyloric rings M2 (or the proximal side of the pyloric ring M2) is a predetermined site of the digestive organs at which the support portions 121 and 122 are disposed while being in contact with the predetermined site; however, the site is not particularly limited to the pyloric ring M2 insofar as the support portions 121 and 122 can be disposed inside the digestive organs. However, with indwelling performance of the digestive tract device 100 being taken into consideration, the site preferably has an inner diameter which is smaller than that of the proximal side and the distal side of the site, and for example, a cardia M7 (refer to FIG. 12) that is the upper part of a stomach M1 is selected as a site other than the pyloric ring M2.

As illustrated in FIG. 4, the holding portion 120 can be configured to include a body portion 123 possessing a substantially elliptical shape; a first end portion 125 that extends from the body portion 123 toward the proximal end side; and a second end portion 126 that extends from the body portion 123 toward the proximal end side. A first neck portion 121 can be formed between the body portion 123 and the first end portion 124, and a second neck portion 122 can be formed between the body portion 123 and the second end portion 125. In the following description of the specification, the first neck portion 121 and the second neck portion 122 may also be referred to as support portions.

The holding portion 120 can be configured such that the overall exterior shape of the holding portion 120 is an Ω shape in a front view. The body portion 123 of the holding portion 120 preferably has a width d that is greater than the diameter of the pyloric ring M2, and the width d can be approximately 10 mm to approximately 70 mm.

Figure 6:
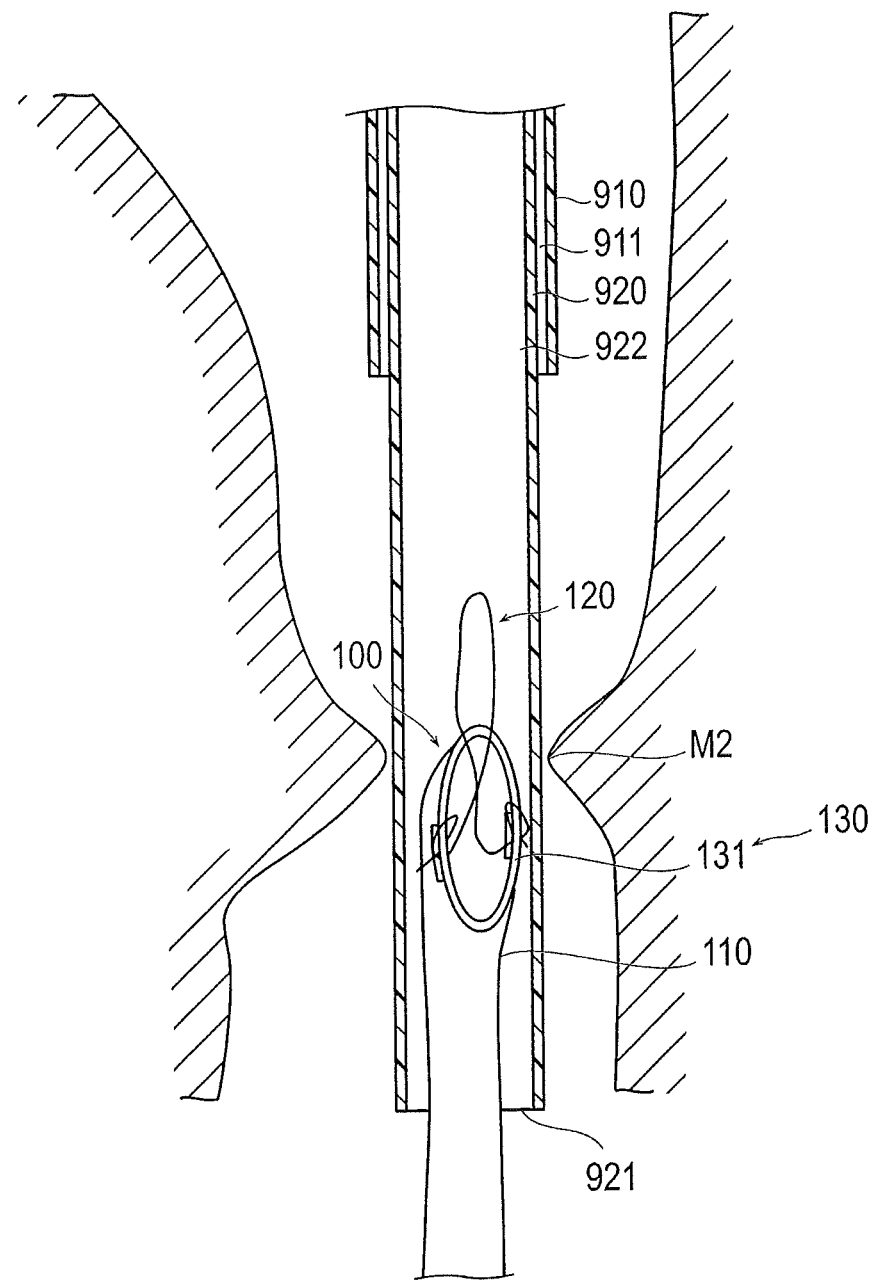
FIG. 6 is a cross-sectional view illustrating the sequence of indwelling the digestive tract device in the first embodiment inside the living body.
Figure 7:
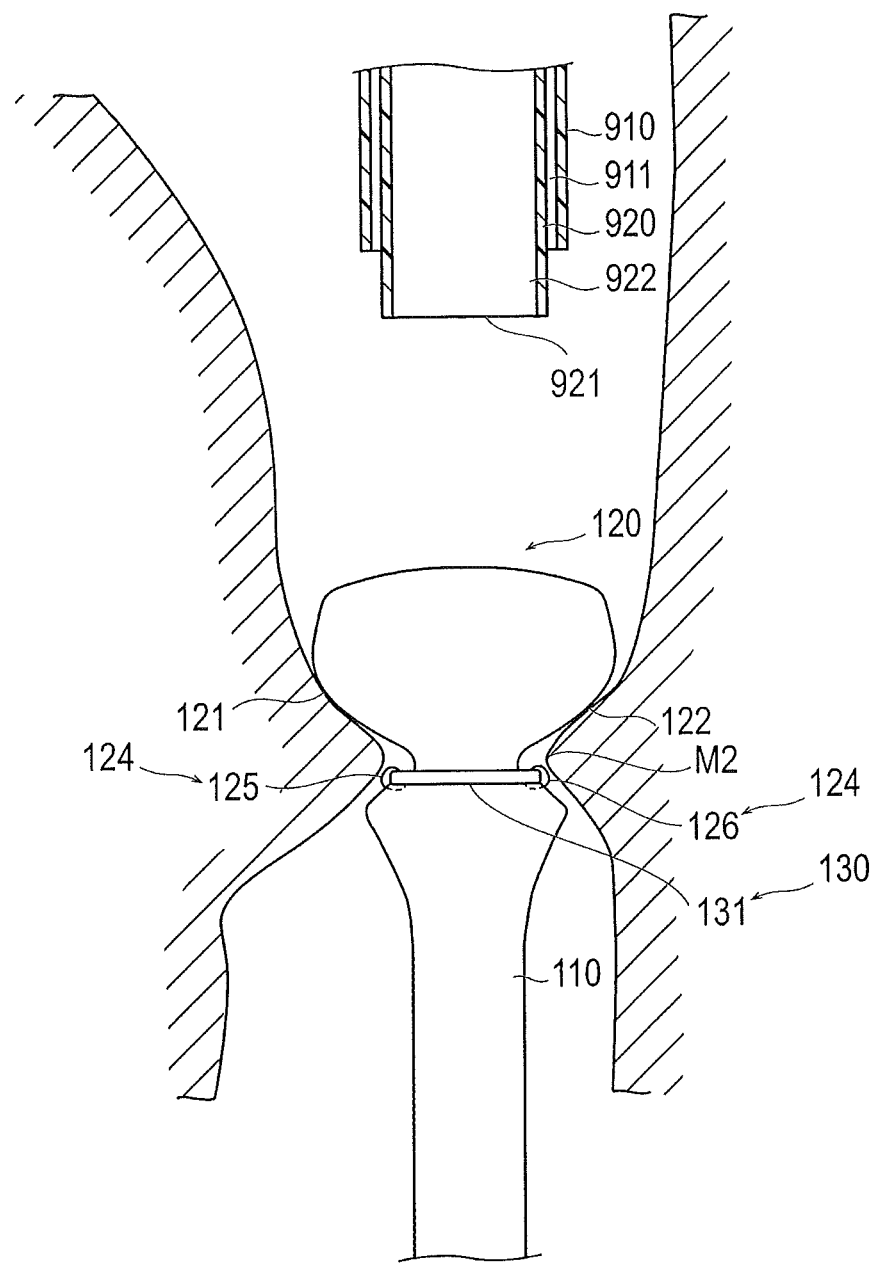
FIG. 7 is a cross-sectional view illustrating the sequence of indwelling the digestive tract device in the first embodiment inside the living body.

The holding portion 120 of the digestive tract device 100 is formed from a shape memory alloy that is pre-formed in an Ω shape. As illustrated in FIG. 6, it is possible to shrink or contract the holding portion 120 into a predetermined shape before indwelling the digestive tract device 100 in the living body, and as illustrated in FIG. 7, the holding portion 120 is configured to be restored to the exterior memory shape of Ω when the digestive tract device 100 is indwelled in the living body. A Ni—Ti alloy, a Cu—Zn—Al alloy, a Fe—Mn—Si alloy, or the like which are well known can be used as the shape memory alloy material. In the embodiment, the entirety of the holding portion 120 is formed from a shape memory alloy so as to be able to smoothly perform an indwelling operation; however, the holding portion 120 can be formed from a metal material, a resin material, or the like which are well known. For example, the same material as that of an annular member 131 (to be described later) can be used as an example of such a material for fabricating the holding portion 120.

As illustrated in FIGS. 2 and 3, the holding portion 120 is engaged with the proximal end side of the tubular portion 110. The holding portion 120 can be engaged with the tubular portion 110 via an engaging portion 130 in such a way that the holding portion 120 can rotate relative to the tubular portion 110. For example, the engaging portion 130 can be formed by the annular member 131 that is attached to the tubular portion 110. An engaging portion 124 of the holding portion 120 is hooked onto and is engaged with the annular member 131, and thus the engagement can be obtained in such a way that the holding portion 120 can rotate relative to the tubular portion 110. For example, the engaging portion 124 of the holding portion 120 can be formed by the first end portion 125 and the second end portion 126 of the holding portion 120.

The engaging portion 124 of the holding portion 120 can be configured to be hooked onto the annular member 131 via a side hole 115 formed in the tubular portion 110. In this configuration, since the engaging portion 124 can smoothly move along the annular member 131, it is possible to smoothly rotate the holding member 120. Since the range of rotation of the holding portion 120 is restricted by the side hole 115, it is possible to prevent excessive rotation of the holding portion 120. For example, as illustrated in FIG. 3, in order to prevent the engaging portion 124 from unintentionally falling away from the tubular portion 110, the engaging portion 124 can be engaged into the side hole 115 by wrapping a portion of the holding portion 120 about the annular member 131 such that a loop portion is formed in the engaging portion 124. The material of the annular member 131 is not limited to a specific material, and the annular member 131 can be formed from a metal material, a resin material, or the like. The following metal materials can be used: SUS; titanium; magnesium; chromium; cobalt; nickel; aluminum; gold; silver; copper; iron; and the like. The following resin materials can be used: polyether ether ketone (PEEK); polyether ketone ketone (PEKK); polycarbonate urethane (PCU); self-reinforced polyphenylene (SRP); a carbon fiber-reinforced polymer or glass fiber-reinforced polymer; ABS; and the like. The annular member 131 can be formed from a predetermined shape memory alloy that is the same as that of the holding portion 120 such that the annular member 131 before being indwelled is shrunk, and the annular member 131 after being indwelled is restored to an annular shape.

As illustrated in FIGS. 1 to 3, the tubular portion 110 is formed in a hollow circular tubular shape with the through hole 111 passing throughout the tubular portion 110 in the longitudinal direction. A proximal end opening 112 is located at the proximal end of the tubular portion 110 so that fluids such as foods or the like flow into the tubular portion 110 via the proximal end opening 112. A distal end opening 113 is located at the distal end of the tubular portion 110 so that fluids such as foods or the like flowing into the tubular portion 110 are discharged to the outside of the tubular portion 110 via the distal end opening 113. A larger-diameter portion 118 can be provided at a predetermined site on the proximal side of the tubular portion 110, and the larger-diameter portion 118 has an outer diameter which is greater than the outer diameter of other sites or places along the tubular portion 110. By virtue of the large-diameter portion 118, fluids flowing into the tubular portion 110 from the stomach M1 can be suitably prevented from flowing into a duodenum M3 (refer to FIG. 4).

In the embodiment, the tubular portion 110 is formed from polytetrafluoroethylene (PTFE); however, the material of the tubular portion 110 is not limited to PTFE insofar as the tubular portion 110 can be flexibly deformed, and polyethylene, silicone resin, polyurethane, or the like may be used.

The thickness of the tubular portion 110 is preferably 0.002 mm to 0.02 mm, the outer diameter of the tubular portion 110110 is preferably 10 mm to 60 mm, the length of the tubular portion 110 along the long axis of the tubular portion direction is preferably 600 mm to 1300 mm. It is to be understood that the dimensions of the tubular portion 110 are not limited to these dimensions.

Hereinafter, an example of the sequence of indwelling the digestive tract device 100 in the first embodiment in the living body will be described.

In FIG. 12, for example, the position in which the digestive tract device 100 is indwelled is in the vicinity of the pyloric ring M2 of the digestive organs. The pyloric ring M2 is positioned between the stomach M1 and the duodenum M3, and the inner diameter of the pyloric ring M2 is smaller than the inner diameters of the stomach M1 and the duodenum M3. The duodenum M3 has a duodenal bulb M4 that is adjacent to the stomach M1, with the pyloric ring M2 interposed between the duodenal bulb M4 and the stomach M1, and a descending part M5 of the duodenum is present on the distal side of the duodenal bulb M4, and has an inner diameter which is smaller than that of the duodenal bulb M4. In the description here, the stomach M1, the pyloric ring M2, the duodenum M3, the cardia M7, and the like are collectively referred to as the digestive organ.

As illustrated in FIG. 6, it is possible to indwell the digestive tract device 100 using an endoscope 910, a catheter 920, or the like which are well known in the medical field. Specifically, the distal end of the endoscope 910 is perorally or pernasally guided to the vicinity of the pyloric ring M2, and the catheter 920 is guided to the pyloric ring M2 via a predetermined channel 911 that is provided in the endoscope 910. The digestive tract device 100 is guided into a lumen 922 of the catheter 920 in a state where the holding portion 120 of the digestive tract device 100 is shrunk or contracted. At this time, the digestive device 100 can be pushed into the lumen 922 of the catheter 920 also using a forceps or the like. It is possible to indwell the digestive tract device 100 by introducing a guide wire which is well known in the medical field into the endoscope 910 along with the catheter 920, and using the guide wire and the catheter 920. In addition, it is possible to indwell the digestive tract device 100 by operating the guide wire and the catheter 920 under X-ray illumination without the aid of the endoscope 910.

After the digestive tract device 100 is guided to a predetermined position, as illustrated in FIG. 7, the digestive tract device 100 is pushed out of a distal end opening 921 of the catheter 920. At this time, the holding portion 120 of the digestive tract device 100 is restored to the pre-memory shape of Ω. The first neck portion 121 serving as a support portion, and the second neck portion 122 serving as support portion come into contact with the pyloric ring M2 (or the vicinity of the pyloric ring M2). The first neck portion 121 and the second neck portion 122 are hooked onto the vicinity of the pyloric ring M2 such that the holding portion 120 is supported by the digestive organ. Since the holding portion 120 is supported, the tubular portion 110 which is engaged with (connected to) the holding portion 120 is held inside the duodenum M3. As a result, as illustrated in FIG. 13, the digestive tract device 100 is indwelled inside the digestive organ.

When the digestive tract device 100 is introduced into the living body, the tubular portion 110 of the digestive tract device 100 can be prepared in a state where the tubular portion 110 is folded in advance (i.e., the tubular portion 110 of the digestive tract device 100 is folded before the digestive tract device 100 is introduced into the living body). After the tubular portion 110 is introduced into the digestive organ, it is possible to temporarily tack an auxiliary member to the distal end side of the tubular portion 110 so as to stimulate the extension of the tubular portion 110 by peristalsis. The auxiliary member can be a spherical member or the like, and can be configured such that when force is applied to the auxiliary member toward the distal side due to peristalsis, the auxiliary member causes the tubular portion 110 to extend, and after the extension of the tubular portion 110 is completed, the auxiliary member is disengaged from the tubular portion 110 due to the force associated with peristalsis, and is finally excreted. The auxiliary member can be tacked to the tubular portion 110 using adhesive, or the auxiliary member is engaged with the tubular portion 110 in a state where the auxiliary member can be detached from the tubular portion 110 by a predetermined force.

Hereinafter, an operation of the digestive tract device 100 will be described with reference to FIGS. 12 and 13.

When the stomach M1 is empty, the stomach M1 contracts and becomes flat, and when foods are ingested, the stomach M1 expands, and the diameter of the stomach M1 is increased. Foods are stirred by contractile waves of the stomach M1, are digested by gastric juices, and are transported to the distal side along with decomposed products such as chyme (fluids). A forecourt part M6 of the pylorus secretes alkaline mucus, and neutralizes acid decomposed products such as chyme. When the decomposed products turn into being alkaline, the sphincter of the pyloric ring M2 is relaxed such that the pyloric ring M2 is opened, and the intestines undergo intestinal motility. The decomposed products are sent into the duodenum M3 via the pyloric ring M2 due to the contraction of the forecourt part M6 of the pylorus which is a lower part of the stomach M1. The duodenum M3 transports the decomposed products to the distal side while stirring the decomposed products via intestinal motility including peristalsis, segmentation movement, and pendular movement.

When a patient with the digestive tract device 100 placed in the digestive organ ingests foods, the foods are digested in the stomach M1, and then decomposed products such as chyme flow into the through hole 111 of the tubular portion 110 from the vicinity of the pyloric ring M2. Since the tubular portion 110 can be flexibly deformed in response to the movement of the digestive organ, the decomposed products flowing into the tubular portion 110 are pushed toward the distal side while being stirred due to the intestinal motility of the duodenum M3. Nutrients do not come into direct contact with the duodenum M3 and the upper part of the jejunum which are covered by the tubular portion 110 and are the upper parts of the small intestine, and the nutrients are absorbed after foods pass through the tubular portion 110. When foods do not come into the upper part of the small intestine, the absorption of nutrients is reduced, and GIP, glucagon, or the like that are gastrointestinal hormones which are secreted due to a stimulus by nutrients are less likely to be secreted. GIP, glucagon, or the like is deemed to be a factor which reduces the amount of secretion of insulin, and since GIP, glucagon, or the like is not secreted, the secretion of insulin is not inhibited, and it is possible to reduce a blood glucose level due to insulin. When undigested foods reach the lower part of the jejunum and the ileum which are the lower parts of the small intestine, GLP-1, that is, a gastrointestinal hormone that is deemed to be a factor that stimulates the secretion of insulin is increasingly secreted due to stimulus by nutrients, and thus the secretion of insulin is further stimulated, and it is possible to reduce a blood glucose level. As such, when the digestive tract device 100 is indwelled in the digestive organ, the digestion and absorption of nutrients is reduced, and a blood glucose level is reduced, and thus the indwelling of the digestive tract device 100 is highly effective in the treatment of diabetes (especially type 2 diabetes) and obesity.

The treatment of diabetes and obesity according to the present invention includes a treatment, heeling, relief, alleviation, change, change for the better, improvement, restoration, enhancement or action of an illness or symptoms of a patient.

As illustrated in FIGS. 4 and 5, when the digestive tract device 100 in the embodiment is indwelled, and then a contractile force is applied to the holding portion 120 due to peristalsis, the neck portions 121 and 122 of the holding portion 120 move in the circumferential direction of the tubular portion 110 while contact between the pyloric ring M2 and the neck portions 121 and 122 is maintained. Due to this movement, the entirety of the holding portion 120 can move along the circumferential direction of the tubular portion 110, and the position of contact between the holding portion 120 and the pyloric ring M2 is changed. When the holding portion 120 moves along the circumferential direction of the tubular portion 110, the engaging portion 130 prevents the rotation of the tubular portion 110 induced by this movement, and thus the tubular portion 110 is prevented from being twisted or kinked.

Also when an external force occurring when fluids flowing into the tubular portion 110 come into contact with the holding portion 120 is applied to the holding portion 120, similarly, the holding portion 120 can move. When an external force induced by peristalsis or fluids is applied to the holding portion 120, the holding portion 120 can not only move in the circumferential direction of the tubular portion 110, but can also move along the inner wall of the pyloric ring M2 in the longitudinal direction of the tubular portion 110.

Hereinafter, an example of the sequence of removing the digestive tract device 100 in the first embodiment from the digestive organ of the living body will be described.

Figure 8:
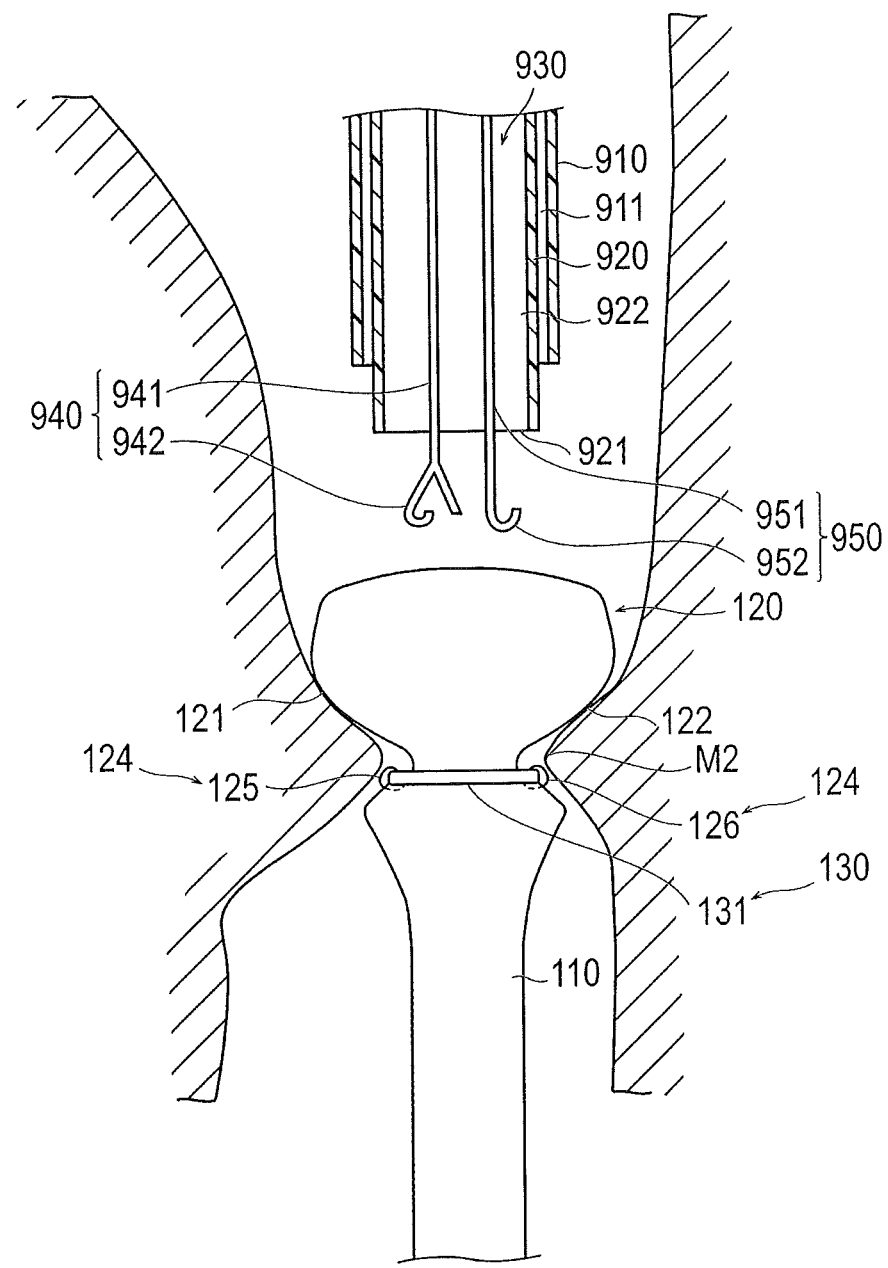
FIG. 8 is a cross-sectional view illustrating the sequence of removing the digestive tract device in the first embodiment from the living body.

As illustrated in FIG. 8, similar to the indwelling operation, it is possible to remove the digestive tract device 100 using the endoscope 910, the catheter 920, and the like which are well known in the medical field. In addition, it is possible to also use a predetermined removal tool 930 along with these medical devices.

An example of the removal tool 930 can be a tool including a pushing tool 940 that is comprised of a long (elongated) body portion 941 and a bifurcated distal end portion 942, and a pulling tool 950 that is made up of a long (elongated) body portion 951 and a curved distal end portion 952. As illustrated, for example, it is possible to configure the pushing tool 940 so that one leg of the bifurcated distal end portion 942 is formed in a substantially J shape, and the other leg is formed in a sloped linear shape; however, in addition to this, it is possible to use a snare or the like which is well known in the medical field.

The material of each of the tools 940 and 950 of the removal tool 930 is not limited to a specific material insofar as the tools 940 and 950 made of the material can be introduced into the digestive organ of the living body, and with the ease of introduction of the body portions 941 and 951 into the living body being taking into consideration, each of the body portions 941 and 951 is preferably formed from a flexible material. Each of the distal end portions 942 and 952 is preferably formed from a hard resin material or a hard metal material so that it is possible to push or pull a predetermined portion of the digestive tract device 100. Each of the body portions 941 and 951 can be formed from polyvinyl chloride, polyethylene, polypropylene, cyclic polyolefin, or the like. Each of the distal end portions 942 and 952 can be formed from SUS, titanium, magnesium, chromium, or the like.

As illustrated in FIG. 8, the operation of removing the digestive tract device 100 from the living body involves, first, pernasally or perorally introducing the distal end of the endoscope 910 to the vicinity of the pyloric ring M2, and the catheter 920 is introduced to the pyloric ring M2 via the channel 991 of the endoscope 910. Subsequently, the distal end portion 942 of the pushing tool 940 and the distal end portion 952 of the pulling tool 950 are introduced to the vicinity of the pyloric ring M2 via the lumen 922 of the catheter 920.

Figure 9:
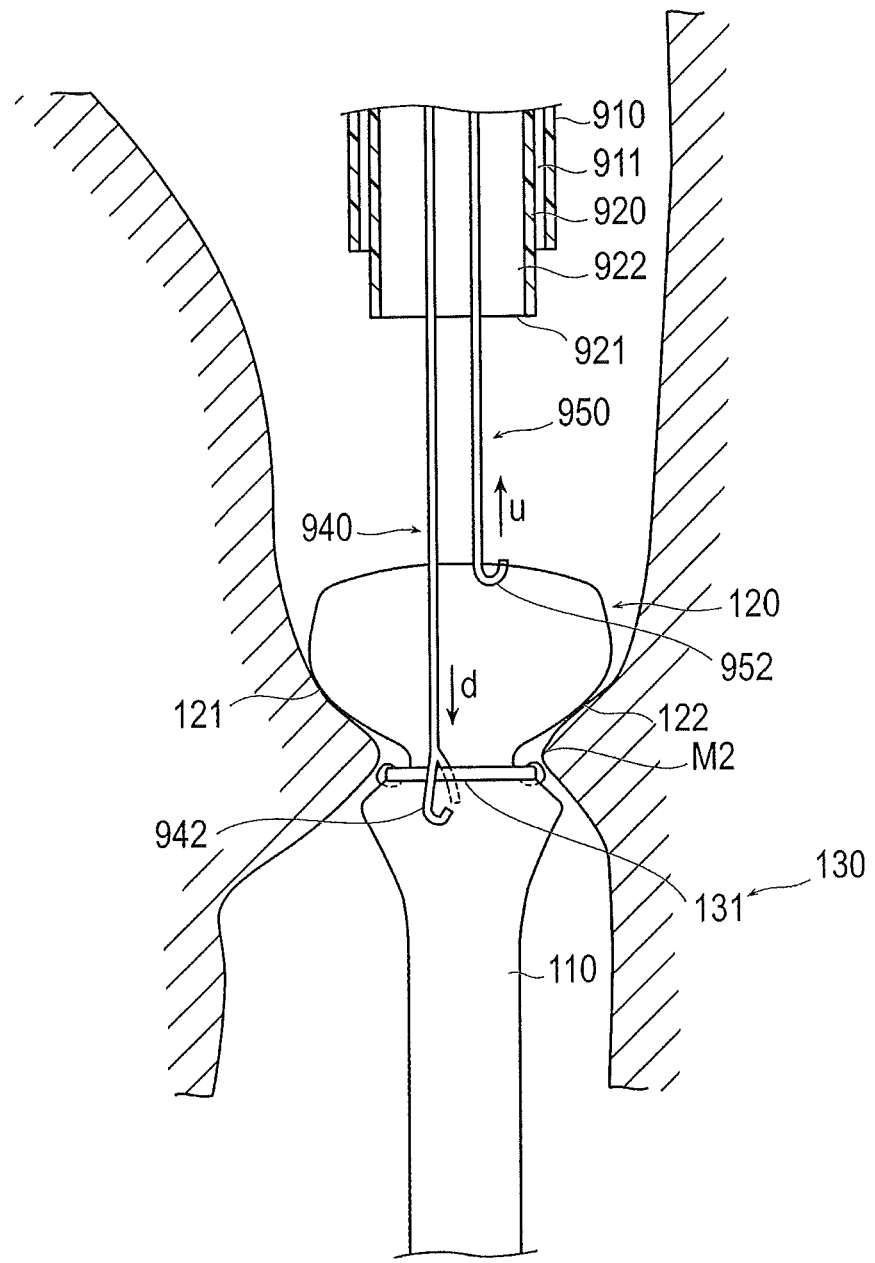
FIG. 9 is a cross-sectional view illustrating the sequence of removing the digestive tract device in the first embodiment from the living body.

Subsequently, as illustrated in FIG. 9, the annular member 131 of the digestive tract device 100 is pushed toward the distal end side using a root portion of the distal end portion 942 of the pushing tool 940 (as illustrated by arrow d in FIG. 9). In contrast, the holding portion 120 is pulled toward the proximal end side using the pulling tool 950 (as illustrated by arrow u in FIG. 9). When the tools 940 and 950 are operated in this way, as illustrated in FIG. 10, the holding portion 120 is deformed to take on an oblong shape or configuration along an axial direction of the tubular portion 110. The annular member 131 is appropriately sloped such that the annular member 131 is detached from the pyloric ring M2.

Subsequently, as illustrated in FIG. 11, the distal end opening 921 of the catheter 920 is brought to the vicinity of the holding portion 120 and the annular member 131, and the holding portion 120 and the annular member 131 are accommodated in the lumen 922 of the catheter 920. It is possible to remove the digestive tract device 100 from the living body by pulling the catheter 920 and the tools 940 and 950 upwards via the channel 911 of the endoscope 910. When the pushing tool 940 with a J-shaped distal end and a linear distal end is used, it is possible to hook the J-shaped distal end of the pushing tool 940 onto the wrapped portion (the loop portion) of the engaging portion 124 of the holding portion 120, and pulling the holding portion 120 upwards.

The method of indwelling and removing the digestive tract device 100 is not limited to a specific method insofar as it is possible to indwell the holding portion 120 on a target site, and to remove the holding portion 120 from the target site using the method, and it is possible to appropriately change the method according to the configuration or the like of the holding portion of the digestive tract device, as will be described in embodiments later.

As such, in the digestive tract device 100 in the embodiment, while being in contact with a plurality of sites (plurality of spaced apart locations) of the digestive organ, the holding portion 120 is supported in such a way that the holding portion 120 holding the tubular portion 110 (into which fluids such as foods or the like flow) relative to the living body can move in the longitudinal direction and the circumferential direction of the tubular portion 110. For this reason, the position of contact between the holding portion 120 and the digestive organ is appropriately changed while the tubular portion 110 is held by the holding portion 120, and thus a contractile force induced by peristalsis, a pulling force induced by the inflow of fluids, or the like can be prevented from being locally applied to a specific site of the digestive organ over time, and an indwelling-induced burden on the living body can be suitably reduced.

Since the holding portion 120 is formed from a wire-like body, it is possible to reduce the area of contact between the holding portion 120 and the digestive organ, and to further reduce an indwelling-induced burden on the living body. Since the support portions 121 and 122 are formed from portions of the wire-shaped body, it is possible to reduce the number of components, and it is possible to reduce manufacturing costs, or to simplify manufacturing operations.

Since the holding portion 120 is engaged with the tubular portion 110 in such a way as to be able to rotate relative to the tubular portion 110, when the holding portion 120 rotates, the rotation of the holding portion 120 can be prevented from being transmitted to the tubular portion 110, which in turn prevents the tubular portion 110 from being twisted and kinked. For this reason, even if the holding portion 120 repeatedly moves, fluids can smoothly flow downwards in the tubular portion 110.

Hereinafter, modification examples of the embodiment will be described. FIGS. 14 to 17 illustrate modification examples regarding the shape of a holding portion, and FIGS. 18 to 20 illustrate modification examples regarding the structure of an engaging portion.

As illustrated in Modification Examples 1 to 3 below, the configuration of a holding portion of the digestive tract device can be changed within the limits that the holding portion can move in at least one direction of the circumferential direction and the longitudinal direction of the tubular portion, and has the support portion which is configured such that the support portion comes into contact with a plurality of sites of the digestive organ. Accordingly, for example, the holding portion can be formed in a shape illustrated in each of the modification examples in addition to the shape of Ω.

Modification Example 1

Figure 14:
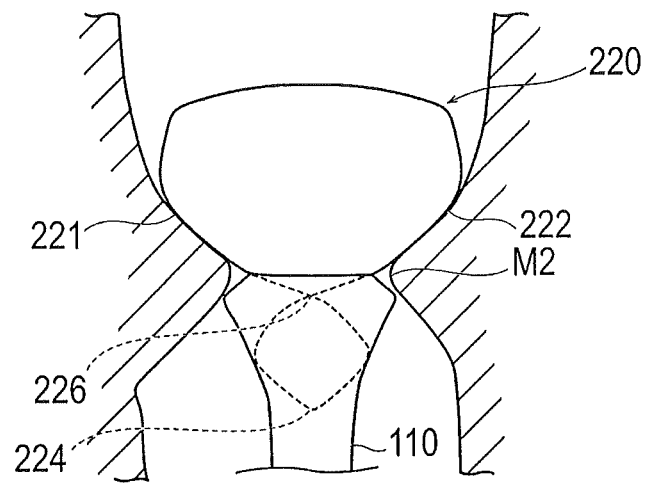
FIG. 14 is a view illustrating Modification Example 1 of the first embodiment.

As illustrated in FIG. 14, the exterior of a holding portion 220 can be formed in a substantially 8 shape such that distal end portions 224 of the holding portion 220 are not open ended, and are continuous with each other. Neck portions 221 and 222 of the holding portion 220 with this configuration serve as support portions which are in contact with the pyloric ring M2, and by which the holding portion 220 is movably supported. Since the distal end portions 224 of the holding portion 220 are not open ended, and are twisted such that the distal end portions 224 intersect each other, when a contractile force is applied to a portion of the holding portion 220 disposed close to the stomach (the upper side in FIG. 14) due to activity of the pyloric sphincter of the stomach, a portion of the holding portion 220 disposed close to the intestine (the lower side in FIG. 14) expands. As a result, it is possible to improve a holding force of the holding portion 220 on the pyloric ring M2. The holding portion 220 and the tubular portion 110 are engaged with each other via the engaging portion 130 in such a way as to be able to rotate relative to each other.

Figure 15:
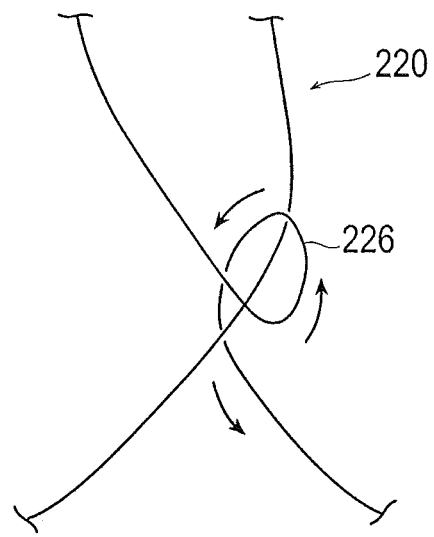
FIG. 15 is an enlarged view illustrating a portion of Modification Example 1.

For example, when the holding portion 220 is formed in a substantially 8 shape, as illustrated in FIG. 15, an intersecting portion 226 can be formed in a loop shape. In this configuration, when the digestive tract device 100 is removed from the living body, it is possible to push the intersecting portion 226 using the distal end portion 942 of the pushing tool 940 (refer to FIG. 9), and thus it is possible to improve the ease of operation of removing the digestive tract device 10.

Modification Example 2

Figure 16:
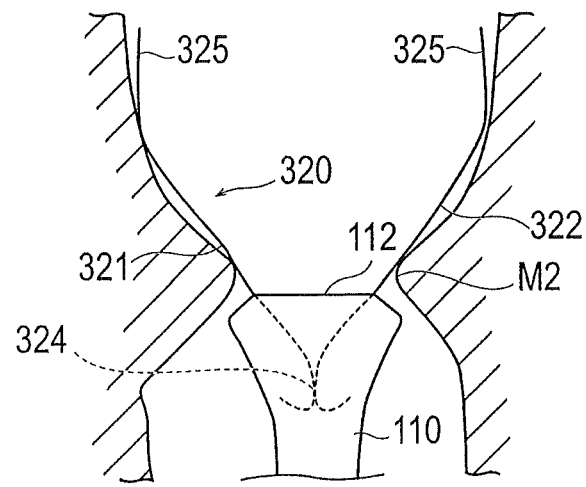
FIG. 16 is a view illustrating Modification Example 2 of the first embodiment.

As illustrated in FIG. 16, the exterior of a holding portion 320 can be formed in a substantially X shape such that proximal end portions 325 of the holding portion 320 are open ended, and distal end portions 324 of the holding portion 320 partially intersect each other. Neck portions 321 and 322 of the holding portion 320 with this configuration serve as support portions which are in contact with the pyloric ring M2, and by which the holding portion 320 is movably supported. For example, the holding portion 320 and the tubular portion 110 can be engaged with each other in such a way as to be able to rotate relative to each other by setting the outer diameter of the distal end portion 324 of the holding portion 320 to be greater than that of the proximal end opening 112 on the proximal end side of the tubular portion 110, and disposing the holding portion 110 in such a way that the proximal end opening 112 of the holding portion 110 is hooked onto the end portions 324.

Modification Example 3

Figure 17:
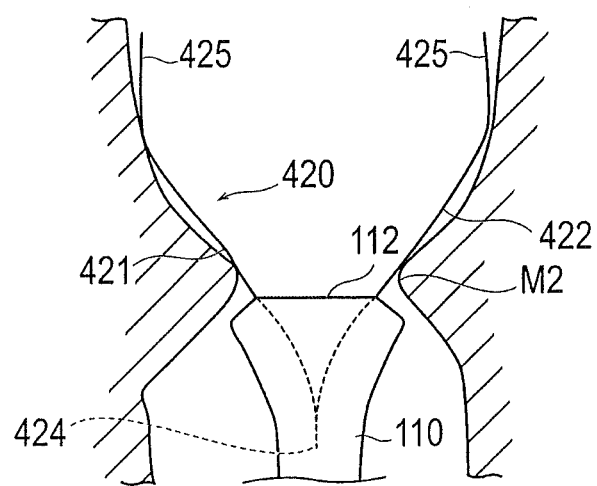
FIG. 17 is a view illustrating Modification Example 3 of the first embodiment.

As illustrated in FIG. 17, the exterior of a holding portion 420 can be formed in a substantially Y shape such that proximal end portions 425 of a holding portion 420 are open ended, and distal end portions 424 of the holding portion 320 are engaged with each other. Neck portions 421 and 422 of the holding portion 420 with this configuration serve as support portions which are in contact with the pyloric ring M2, and by which the holding portion 420 is movably supported. It is possible to adopt the same method as described in Modification Example 2 as a method of engaging the holding portion 420 with the tubular portion 110.

Hereinafter, Modification Examples 4 to 6 relate to the configuration of an engaging portion through which the holding portion and the tubular portion of the digestive tract device are engaged with each other in such a way as to be able to rotate relative to each other. The configuration of the engaging portion which engages the holding portion with the tubular portion is not limited to a specific configuration insofar as the tubular portion can be prevented from being twisted and kinked when the holding portion moves in the circumferential direction of the tubular portion. For example, as illustrated in Modification Examples 4 to 9, it is possible to prevent the tubular portion from being twisted or kinked by engaging the holding portion with the tubular portion using a plurality of annular members.

Modification Example 4

Figure 18A:
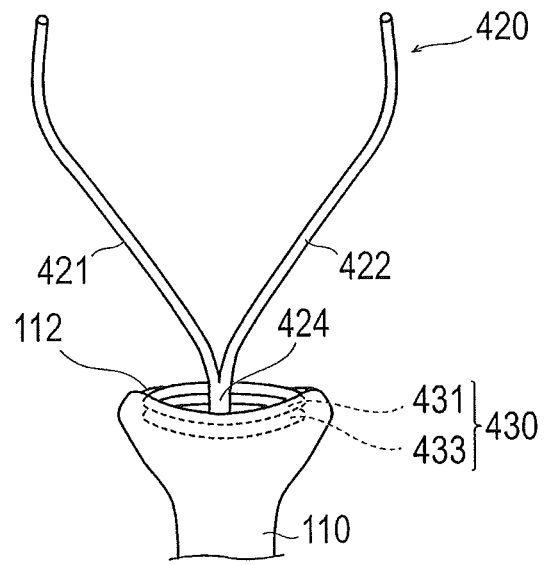
FIG. 18A is a view illustrating Modification Example 4 of the first embodiment.

As illustrated in FIG. 18A, an engaging portion 430 which engages the holding portion 420 with the tubular portion 110 can be configured to include a tubular portion-side annular member 431 attached to the tubular portion 110, and a holding portion-side annular member 433 which is attached to the holding portion 420, and is engaged with the tubular portion-side annular member 431 in such a way that the holding portion-side annular member 433 can rotate relative to the tubular portion-side annular member 431.

For example, the Y-shaped holding portion illustrated in Modification Example 3 can be used as the holding portion 420, and other holding portions with shapes described in other modification examples or the like can be used.

The holding portion-side annular member 433 is fixed to the holding portion 420 using bonding, fusion bonding, welding, or the like. For example, the tubular portion 110 and the tubular portion-side annular member 431 can be disposed such that the outer diameter of the tubular portion-side annular member 431 is greater than that of the proximal end opening 112 on the proximal end side of the tubular portion 110, and the proximal end opening 112 of the holding portion 110 is hooked onto the tubular portion-side annular member 431. The tubular portion-side annular member 431 is disposed while being mounted on the holding portion-side annular member 433. Since the holding portion-side annular member 433 is not fixed to the tubular portion-side annular member 431, both the annular members 431 and 433 can be engaged with each other in such a way as to be able to rotate relative to each other.

Since the holding portion 420 is movably supported by the pyloric ring M2 via the support portions (neck portions) 421 and 422 of the holding portion 420, the tubular portion 110 is also held by the pyloric ring M2 via the tubular portion-side annular member 431 that is disposed while being hooked onto the holding portion-side annular member 433. When an external force induced by peristalsis or fluids is applied to the digestive tract device 10, the holding portion 420 rotates independent of the tubular portion 110, or the tubular portion 110 rotates independent of the holding portion 420. Accordingly, it is possible to prevent the rotation of the tubular portion 110 associated with the movement of the holding portion 420, and it is possible to suitably prevent the tubular portion 110 from being twisted or kinked.

The position of attachment between the holding portion 420 and the holding portion-side annular member 433, and the position of attachment between the tubular portion 110 and the tubular portion-side annular member 431 can be arbitrarily set such that relative rotation between the annular members 431 and 433 is not inhibited. For example, as illustrated in FIG. 18A, the distal end portion 424 of the holding portion 420 can be fixed to the inner circumferential surface of the holding portion-side annular member 433, and the proximal end opening 112 on the proximal end side of the tubular portion 110 can be disposed so as to surround the outer circumferential surface of the tubular portion-side annular member 431, and be attached to the outer circumferential surface.

Figure 18B:
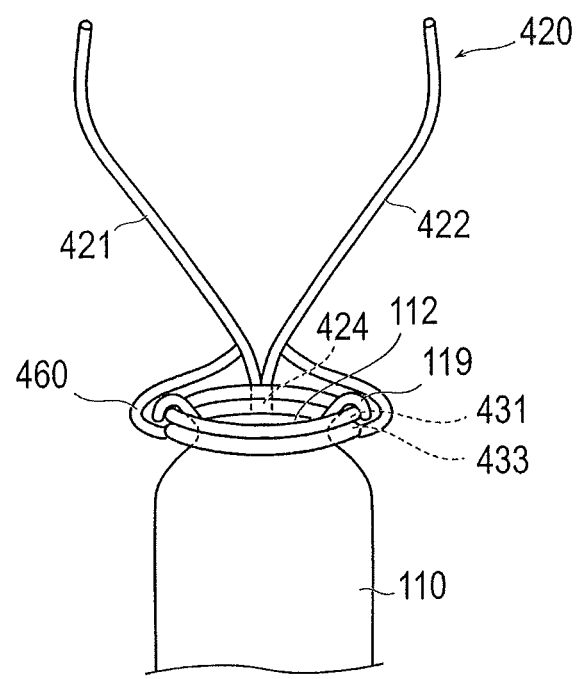
FIG. 18B is a view illustrating another form of Modification Example 4 of the first embodiment.

For example, as illustrated in FIG. 18B, instead of the positions of attachment described above, the holding portion 420 can be attached to the outer circumferential surface of the holding portion-side annular member 433, and the tubular portion 110 can be attached to the inner circumferential surface of the tubular portion-side annular member 431. The holding portion 420 can be attached to the holding portion-side annular member 433 via a connecting member 460 (which is provided at an arbitrary position in the holding portion 420) by well-known methods such as bonding, fusion bonding and the like. For example, as illustrated, it is possible to use the curved connecting member 460 made of a predetermined metal material or a predetermined resin material.

It is possible to form a claw portion 119 at the proximal end of the tubular portion 110, and to attach the tubular 110 to the tubular portion-side annular member 433 via the claw portion 119. The material of the claw portion 119 of the tubular portion 110 is not limited to a specific material insofar as the tubular portion 110 can be engaged with the tubular portion-side annular member 431, and the claw portion 119 can be formed from a metal material, a resin material, or the like. The exterior shape of the claw portion 119 is not limited to a specific shape insofar as the tubular portion 110 can be attached to the tubular portion-side annular member 431 via the claw portion 119.

Modification Example 5

Figure 19A:
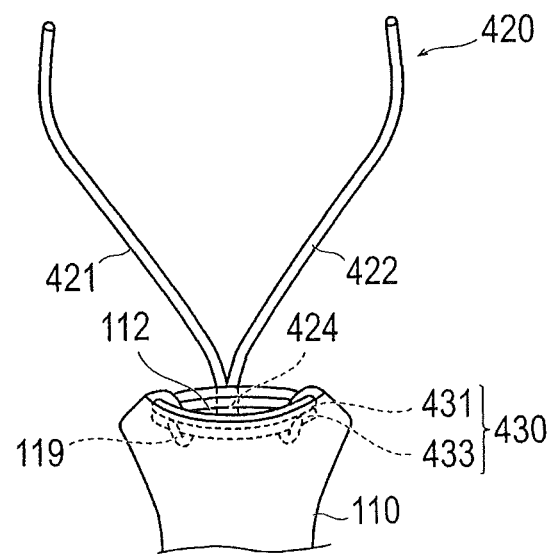
FIG. 19A is a view illustrating Modification Example 5 of the first embodiment.
Figure 20:
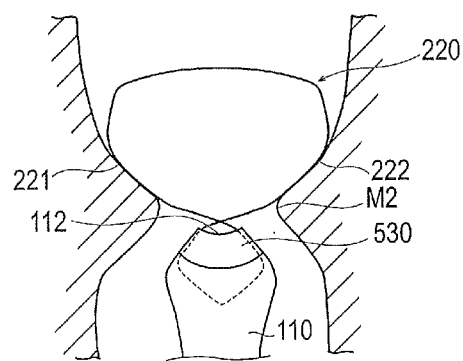
FIG. 20 is a view illustrating Modification Example 6 of the first embodiment.

As in Modification Example 5 illustrated in FIG. 19A, for example, the tubular portion 110 can be attached to the tubular portion-side annular member 431 via the claw portion 119 that is provided on the proximal end side of the tubular portion 110. The tubular portion 110 is attached to an inner circumferential surface of the tubular portion-side annular member 431 via the claw portion 119, and is engaged with the holding portion 420 via the tubular portion-side annular member 431 and the holding portion-side annular member 433. Similar to Modification Example 4, since the holding portion-side annular member 433 is disposed while being mounted on the tubular portion-side annular member 431, both the annular members 431 and 433 can rotate relative to each other. For example, it is possible to fix the holding portion 420 to the holding portion-side annular member 433 by fixing the distal end portion 424 of the holding portion 420 to the outer circumferential surface of the holding portion-side annular member 433 in such a way that relative rotation between the annular members 431 and 433 is not inhibited.

Also when the engaging portion 430 is adopted as illustrated in this modification example, it is possible to prevent the rotation of the tubular portion 110 associated with the movement of the holding portion 420, and to suitably prevent the tubular portion 110 from being twisted or kinked.

Figure 19B:
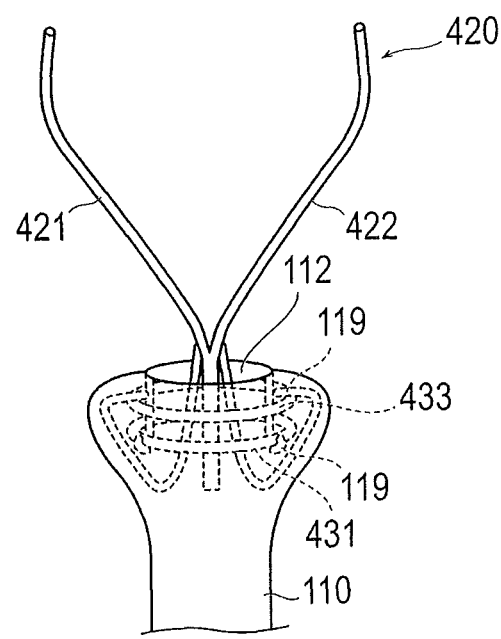
FIG. 19B is a view illustrating another form of Modification Example 5 of the first embodiment.

The claw portion 119 can also be formed in the holding portion 420. For example, as illustrated in FIG. 19B, the holding portion 420 can be attached to the holding portion-side annular member 433 via the claw portion 119 that is formed in the holding portion 420. In contrast, the tubular portion 110 can be attached to the tubular portion-side annular member 431 via the claw portion 119 that is formed in the tubular portion 110. As illustrated, since the claw portions 119 are formed in both the holding portion 420 and the tubular portion 110, and the holding portion 420 and the tubular portion 110 are respectively attached to the annular members 431 and 433, the holding portion 420 and the tubular portion 110 can rotate 360° independent of each other in the circumferential direction. As a result, it is possible to more suitably prevent the tubular portion 110 from being twisted or kinked. In FIG. 19B, for ease of understanding, the gap between the tubular portion-side annular member 431 and the holding portion-side annular member 433 is illustrated; however, actually, similar to the example in FIG. 19A, the holding portion-side annular member 433 is mounted on the tubular portion-side annular member 431.

Figure 19C:
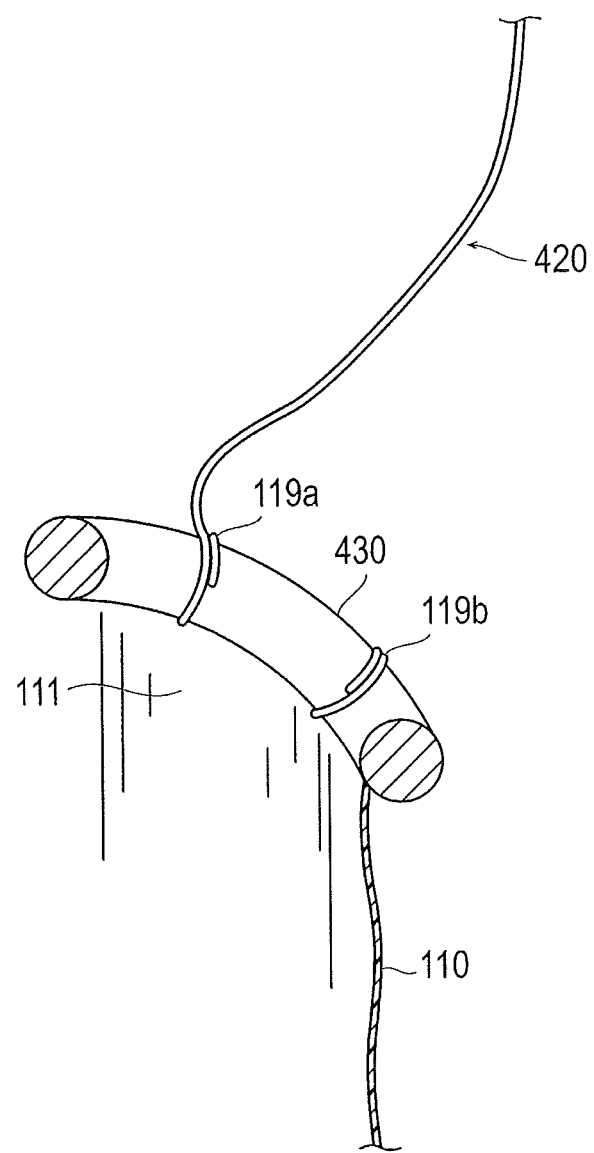
FIG. 19C is a partial cross-sectional view illustrating still another form of Modification Example 5 of the first embodiment.

For example, as illustrated in FIG. 19C, both the holding portion 420 and the tubular portion 110 can be attached to a single engaging member 430 in an annular shape. As illustrated, since the holding portion 420 is attached to the engaging member 430 via a claw portion 119a that is formed in the holding portion 420, and the tubular portion 110 is attached to the engaging member 430 via a claw portion 119b that is formed in the tubular portion 110, the holding portion 420 and the tubular portion 110 can rotate independent of each other. Since the engaging member 430 can be formed from a single member, it is possible to reduce the number of components, and to manufacture the digestive tract device 10 with a simpler configuration.

Modification Example 6

An engaging portion through which the holding portion and the tubular portion are engaged with each other in such a way to be able to rotate relative to each other can be formed from members other than an annular member.

In Modification Example 6 illustrated in FIG. 20, the holding portion with an 8 shape illustrated in Modification Example 1 is used as the holding portion 220. The proximal end opening 112 of the tubular portion 110 is disposed so as to partially cover the distal end side of the holding portion 220. An engaging portion which engages the holding portion 220 with the tubular portion 110 is formed from throttling means 530 that is disposed on the proximal end side of the tubular portion 110. The tubular portion 110 is engaged with the holding portion 220 in a state where the tubular portion 110 can be allowed to rotate by the throttling means 530. For example, the throttling means 530 can be formed from an elastic engaging member, or be formed from a non-elastic engaging member that engages the holding portion 220 with the tubular portion 110. The following materials can be used as the elastic engaging member: an elastic material (a rubber band); a magnetic band that can be expanded and contracted by the action of a magnetic force; and the like. The following materials can be used as the non-elastic engaging member: a suture; a string; a hook; a button; a zipper; a magnetic; and the like.

Also when the engaging portion which is formed from the throttling means 530 as illustrated in this modification example is adopted, it is possible to prevent the rotation of the tubular portion 110 associated with the movement of the holding portion 220, and to suitably prevent the tubular portion 110 from being twisted or kinked.

Hereinafter, a digestive tract device in a second embodiment will be described. Features in this embodiment that are the same as in the embodiment and modification examples described above are identified by common reference numerals and a detailed description of such features is not repeated.

Figure 21:
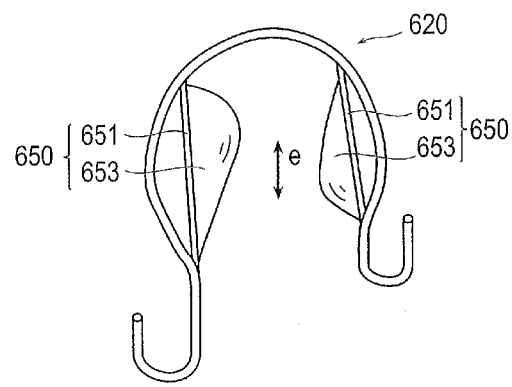
FIG. 21 is a perspective view illustrating a holding portion of a digestive tract device in a second embodiment.

As illustrated in FIG. 21, the digestive tract device in this embodiment includes a movable blade to which an external force is applied, and which induces the movement of the holding portion. The digestive tract device in this embodiment is different from the digestive tract device in the first embodiment in that the digestive tract device includes the movable blade.

A movable blade 650 can be configured to include a fixed member 651 fixed to a predetermined position on a holding portion 620, and a blade portion 653 attached to the fixed member 651. The fixed member 651 is a member that is provided to be able to attach the blade portion 653 to the holding portion 620, and is fixed to the holding portion 620 by, for example, a mechanical method such as bonding, welding, fusion bonding, fitting, or screwing. The material of the fixed member 651 is not limited to a specific material, and can be formed from a metal material or a resin material which are well known.

The blade portion 653 of the movable blade 650 can be made by processing the aforementioned materials of the tubular portion 110 in the shape of a film.

The movable blade 650 is a member that is provided to allow the holding portion 620 to smoothly move when an external force is applied to the holding portion 620. The number or the like of the movable blades provided is not limited to a specific number, and a set of the movable blades 650 can be disposed at different positions on the holding portion 620.

Each of the movable blades 650 can be disposed while extending in the longitudinal direction (a vertical direction illustrated by arrow e in FIG. 21). Each of the movable blades 650 can be twisted around a longitudinal direction of the holding portion 620 such that a vertical force is relatively easily applied to each of the movable blades 650.

The tubular portion 110 is not illustrated in FIG. 21; however, the tubular portion 110 can be engaged with the holding portion 620 via various engaging portions described in the first embodiment, the modification examples and the like.

The operation of the digestive tract device with the holding portion 620 in the second embodiment will be described.

When an external force induced by peristalsis or fluids is applied to the holding portion 620, the external force is applied to the movable blades 650 of the holding portion 620, and thus the holding portion 620 is caused to be able to move (be driven). In particular, when an external force induced by the inflow of fluids into the tubular portion 110 is applied to the holding portion 620, the holding portion 620 is able to move in the circumferential direction of the tubular portion 110 even if a smaller external force is applied.

As such, in the digestive tract device in the second embodiment, the movable blades 650 of the holding portion 620 cause the holding portion 620 to be able to move, and thus it is possible to more suitably prevent a burden from being locally applied to a specific site of the pyloric ring M2 while the digestive tract device is indwelled.

Modification Example

Hereinafter, a modification example of the digestive tract device in the second embodiment will be described. Features in this modification example that are the same as in the second embodiment are identified by common reference numerals and a detailed description of such features is not repeated.

Figure 22:
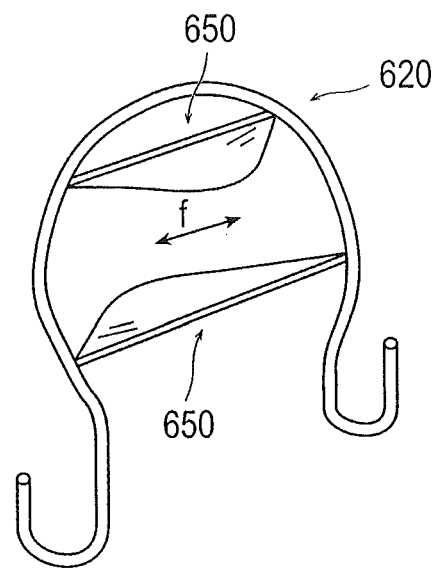
FIG. 22 is a perspective view illustrating a modification example of the holding portion of the digestive tract device in the second embodiment.

As illustrated in FIG. 22, for example, each of the movable blades 650 can be disposed while extending in a lateral direction (rightward and leftward direction illustrated by arrow f in FIG. 22) of the holding portion 620. Each of the movable blades 650 can be twisted around the axis in the lateral direction of the holding portion 620 such that a vertical force is easily applied to each of the movable blades 650.

Also when the movable blades 650 are disposed as illustrated in FIG. 22, similar to the case in which the movable blades 650 are disposed as illustrated in FIG. 21, an external force induced by peristalsis or fluids is applied to the movable blades 650, and thus the holding portion 620 is able to move. In particular, when an external force induced by the inflow of fluids into the tubular portion 110 is applied to the holding portion 620, the holding portion 620 is able to move in the circumferential direction of the tubular portion 110 even if a smaller external force is applied.

In the description of the digestive tract device in the second embodiment illustrated in FIGS. 21 and 22, the movable blades 650 are provided on the holding portion 620 possessing the shape of Q; however, a holding portion with any one of the shapes described in the first embodiment and the modification examples can be used as the holding portion 620. The number, the positions and the like of the movable blades 650 are not limited to a specific number and specific positions illustrated, and for example, it is possible to install the movable blade 650 disposed in the longitudinal direction, and the movable blade 650 disposed in the lateral direction in a combination manner.

Third Embodiment

Hereinafter, a digestive tract device in a third embodiment will be described. Features in this embodiment that are the same as in the first embodiment, the modification examples and the second embodiment are identified by common reference numerals and a detailed description of such features is not repeated.

Figure 23:
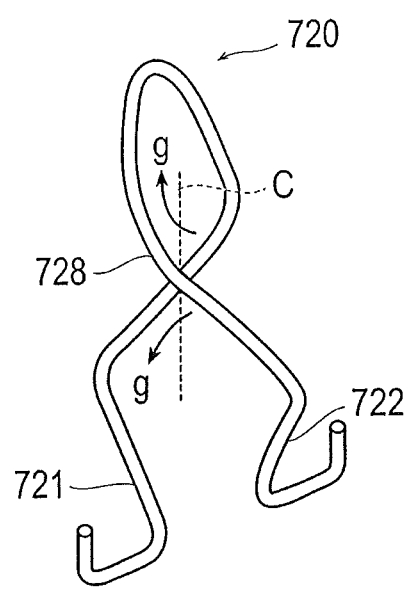
FIG. 23 is a perspective view illustrating a holding portion of a digestive tract device in a third embodiment.

As illustrated in FIG. 23, a holding portion of the digestive tract device in this embodiment includes a twisted portion that is formed by twisting a wire-shaped body (which forms the holding portion) around an axis along the longitudinal direction of the tubular portion. In this regard, the digestive tract device in this embodiment is different from the digestive tract devices in the aforementioned embodiments.

A holding portion 720 includes a twisted portion 728 that is formed by twisting a wire-like body (which forms the holding portion 720) around an axis (reference axis c) along the longitudinal direction of the tubular portion 110 (arrow g illustrates a direction in which the wire-like body is twisted). Neck portions 721 and 722 serving as support portions are formed at predetermined positions on the proximal end side of the holding portion 720.

In a case where the twisted portion 728 is formed in the holding portion 720 as in this embodiment, since the neck portions 721 and 722 can rather easily move when an external force is applied to the holding portion 720, the holding portion 720 can move in the circumferential direction of the tubular portion 110 even if a smaller force is applied. For this reason, it is possible to more suitably prevent a burden from being locally applied to a specific site on the pyloric ring M2 while the digestive tract device is indwelled.

The formation position of the twisted portion 728 and the amount of twisting (the amount of rotation around the reference axis c) required to form the twisted portion 728 are not limited to a specific position and a specific amount of twisting insofar as the holding portion 720 can easily move.

Modification Example

Figure 24:
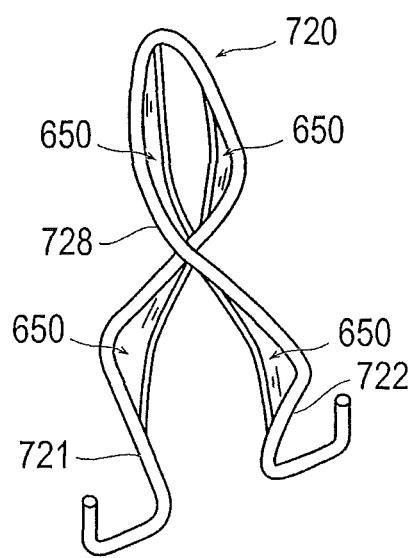
FIG. 24 is a perspective view illustrating a modification example of the holding portion of the digestive tract device in the third embodiment.

Hereinafter, a modification example of the digestive tract device in the third embodiment will be described. Features in this modification example that are the same as in the third embodiment are identified by common reference numerals and a detailed description of such features is not repeated As illustrated in FIG. 24, the movable blades 650 described in the second embodiment are installed on the holding portion 720 of the digestive tract device of the modification example in the third embodiment. Since the movable blades 650 are installed, the movable blades 650 and the twisted portion 728 of the holding portion 720 cause the holding portion 720 to be able to move even if a small external force is applied. For this reason, it is possible to more suitably prevent a burden from being locally applied to a specific site on the pyloric ring M2 while the digestive tract device is indwelled.

In the description of the digestive tract device in the third embodiment illustrated in FIGS. 23 and 24, the twisted portion 728 is formed in the holding portion 720 with the shape of Ω; however, a holding portion with any one of the shapes described in the modification examples of the first embodiment can be used as the holding portion 720. The number, the positions and the like of the movable blades 650 are not limited to a specific number and specific positions, and for example, it is possible to install the movable blade 650 disposed in the longitudinal direction, and the movable blade 650 disposed in the lateral direction in a combination manner. The tubular portion 110 is not illustrated in FIGS. 23 and 24; however, similar to the digestive tract device in the first embodiment, the tubular portion 110 can be engaged with the holding portion 720 via various engaging portions described in the first embodiment, or without the aid of the engaging portions.

Hereinafter, an example of the sequence of indwelling the digestive tract device in the third embodiment illustrated in FIG. 23 in the digestive organ of the living body, and the sequence of removing the digestive tract device from the digestive organ of the living body will be described.

The digestive tract device in the third embodiment can be indwelled or removed using the same methods (refer to FIGS. 6 to 11) described in the first embodiment, and it is possible to adopt a more suitable method while taking the twisted portion 728 of the holding portion 720 into consideration.

Figure 25:
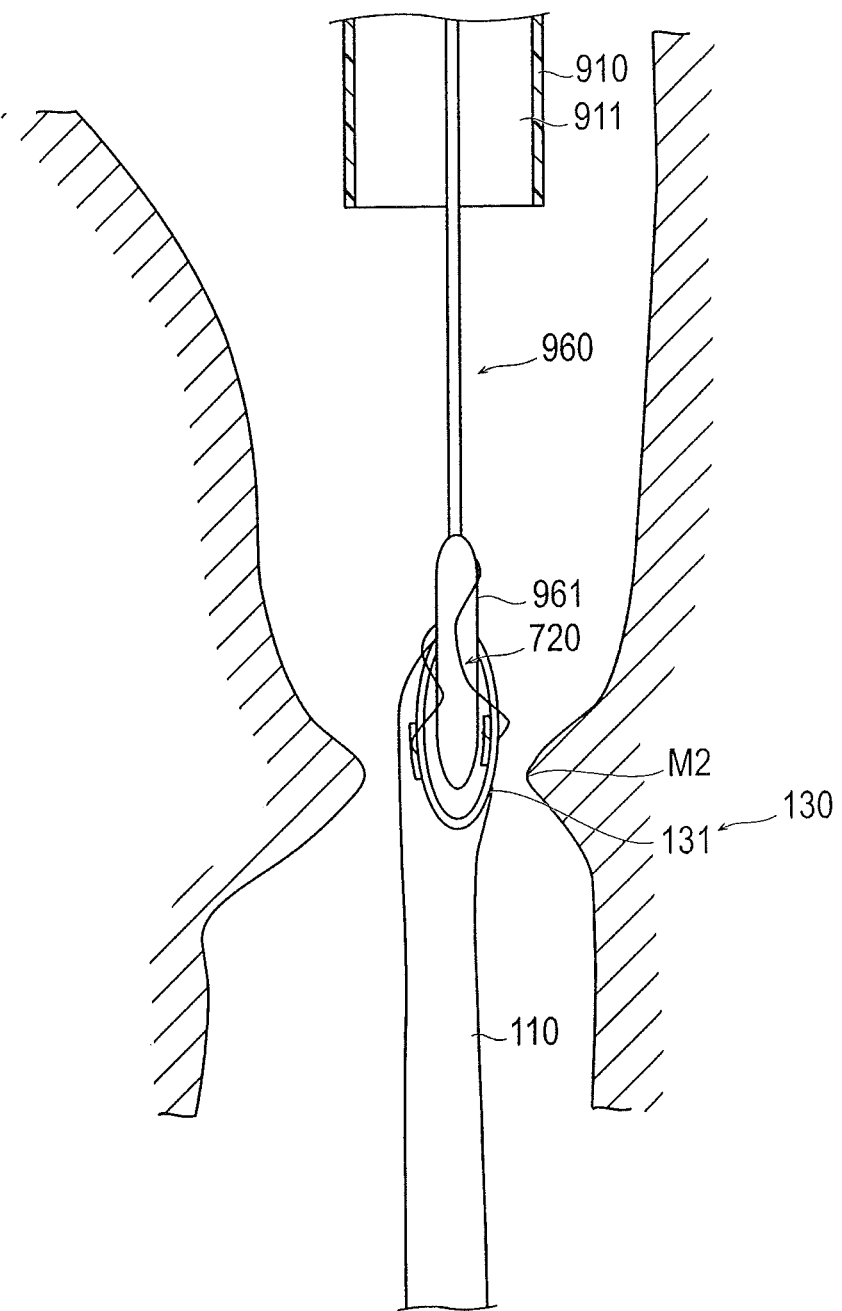
FIG. 25 is a cross-sectional view illustrating the sequence of indwelling the digestive tract device in the third embodiment in the living body.

As illustrated in FIG. 25, an indwelling operation can be performed using a balloon catheter 960 which is well known in the medical field. Before the digestive tract device is guided to the digestive organ, the holding portion 720 is held while being wrapped around the outer circumference of a balloon 961 of the balloon catheter 960. An operator protrudes the balloon 961 (which is contracted via the channel 911 of the endoscope 910) from the distal end of the channel 911 of the endoscope 910 (i.e., axially moves the balloon distally beyond the distal end of the channel 911 of the endoscope 910).

Figure 26:
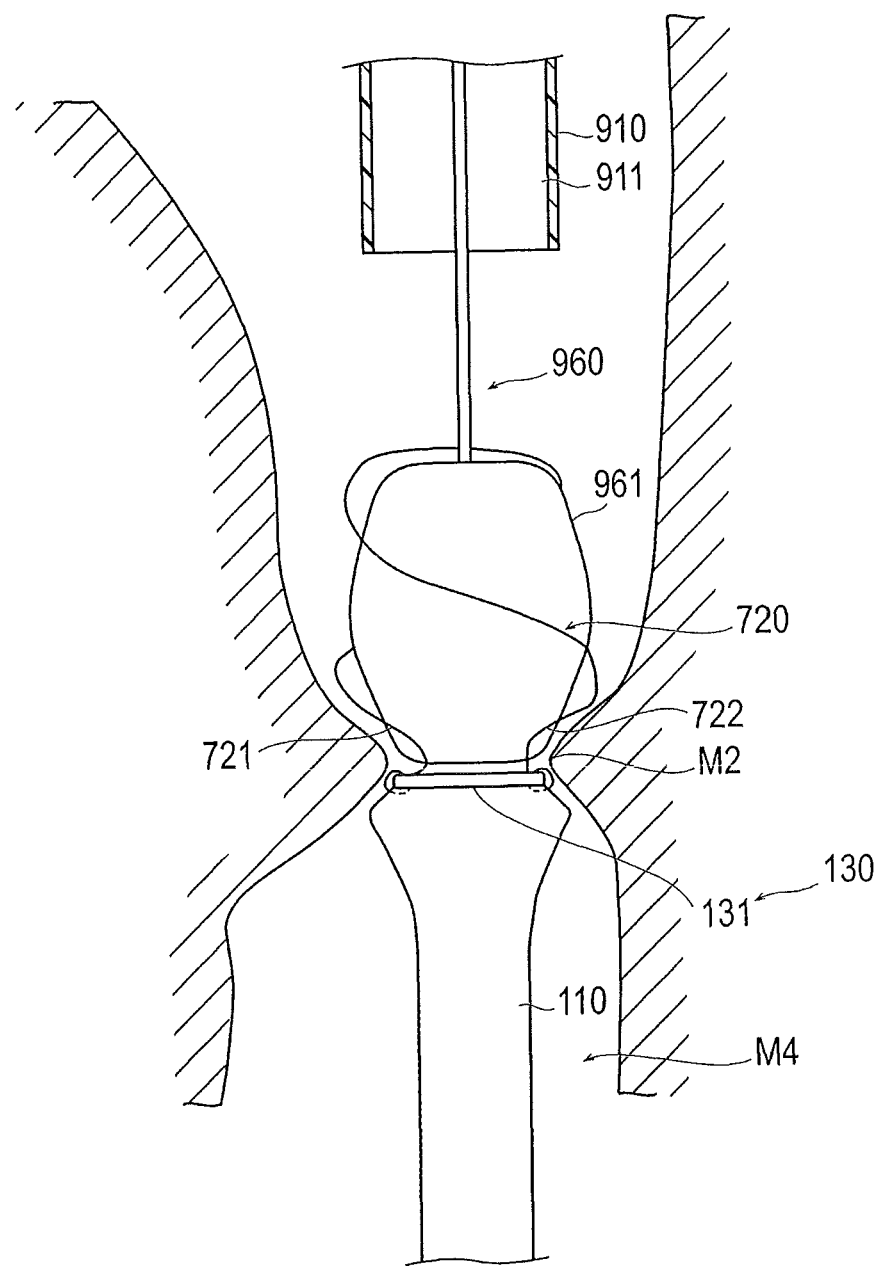
FIG. 26 is a cross-sectional view illustrating the sequence of indwelling the digestive tract device in the third embodiment in the living body.

Subsequently, as illustrated in FIG. 26, the operator expands the balloon 961 via an operation (inflation) by the hands. When the balloon 961 is expanded, the operator positions the neck portions 721 and 722 of the holding portion 720 in the vicinity of the pyloric ring M2, and positions the proximal end side of the tubular portion 110 on the duodenal bulb M4.

Figure 27:
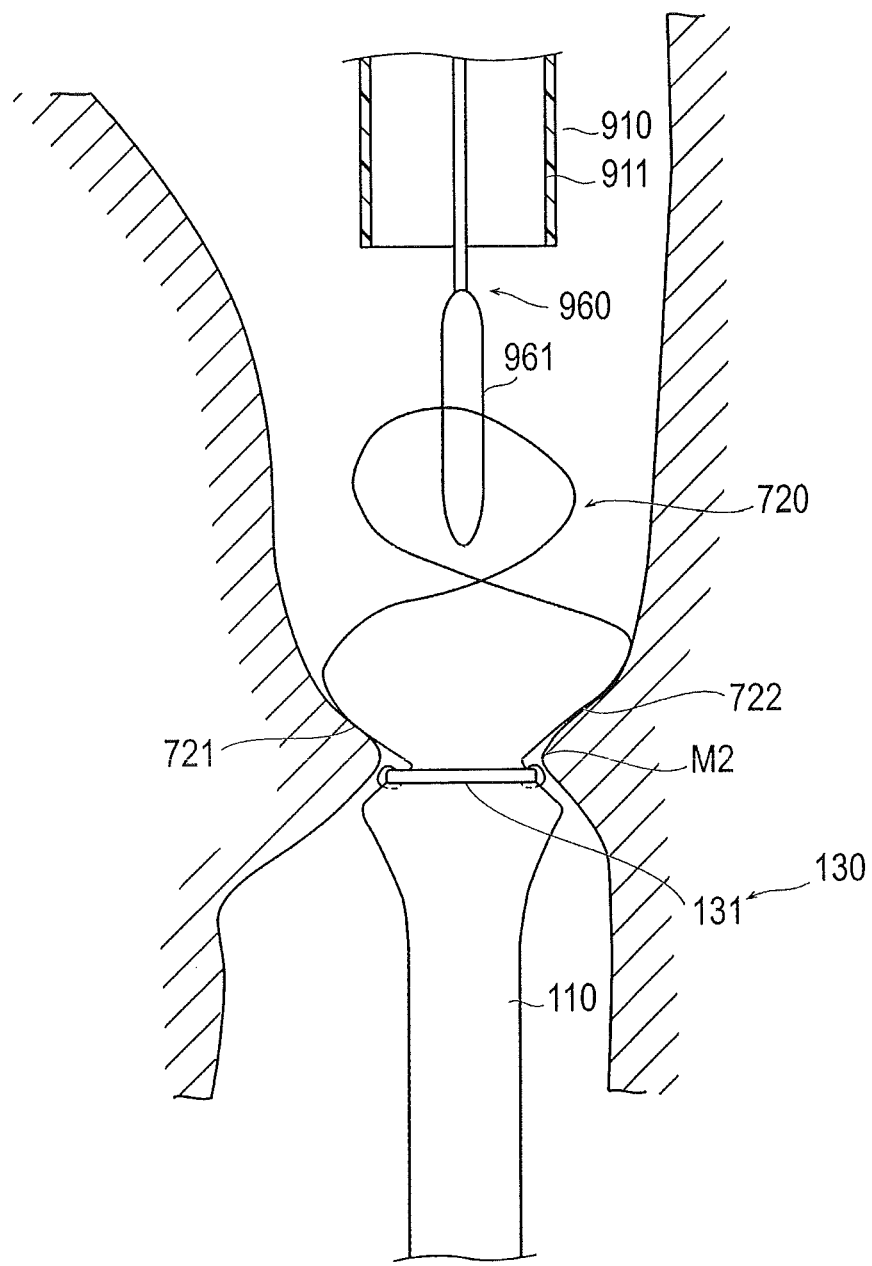
FIG. 27 is a cross-sectional view illustrating the sequence of indwelling the digestive tract device in the third embodiment in the living body.

As illustrated in FIG. 27, the operator hooks the neck portions 721 and 722 of the holding portion 720 onto the pyloric ring M2 such that the entirety of the digestive tract device is held by the digestive organ. After the operator confirms that the digestive tract device is held by the digestive organ, the operator contracts the balloon 961 via an operation (deflation) by the hands. After the aforementioned operations, the operator ends the indwelling operation by removing the balloon catheter 960 and the endoscope 910 from the digestive organ.

Figure 28:
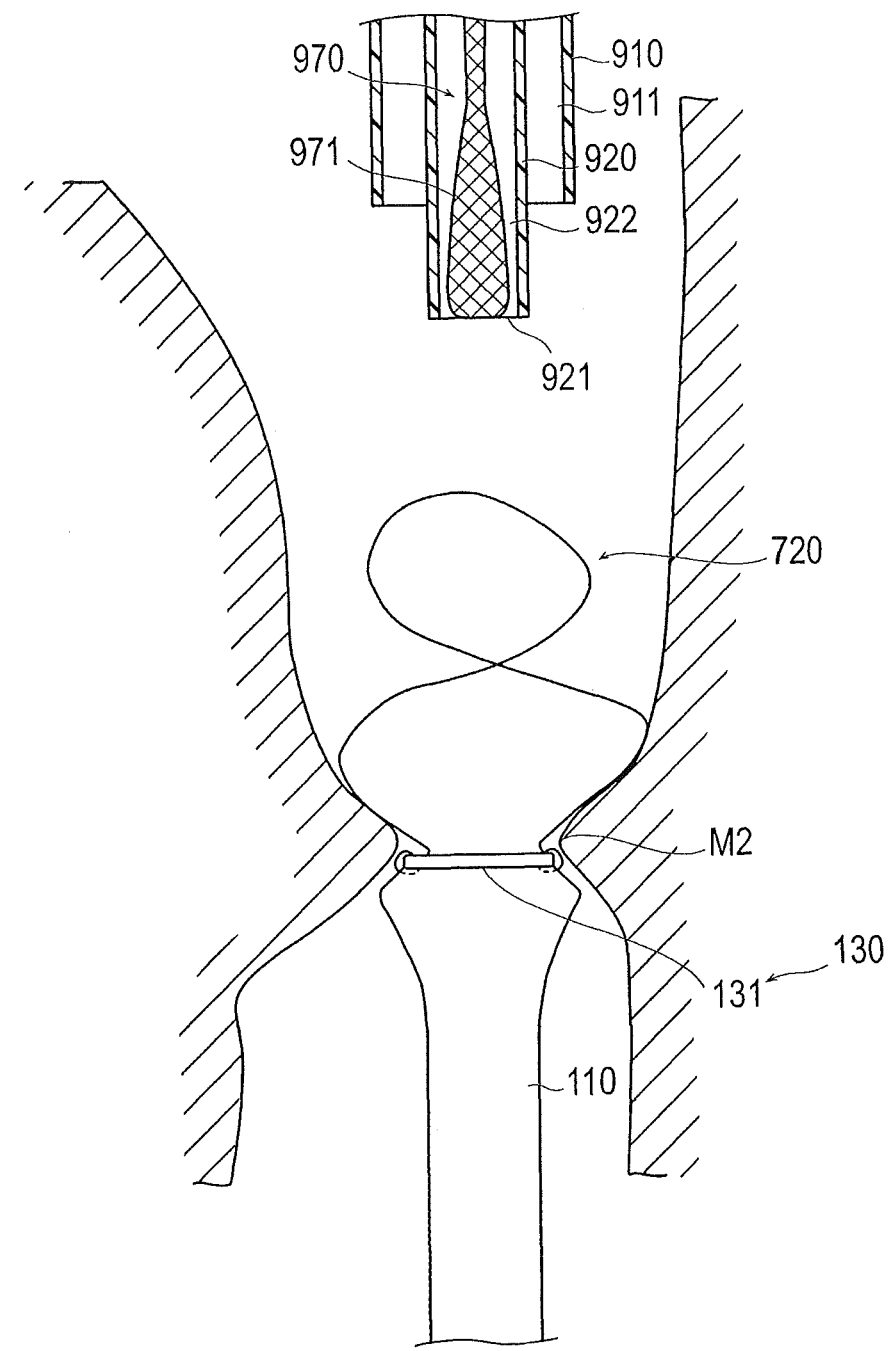
FIG. 28 is a cross-sectional view illustrating the sequence of removing the digestive tract device in the third embodiment from the living body.

As illustrated in FIG. 28, an operation of removing the digestive tract device can be performed using a stent collecting tool 970. First, the stent collecting tool 970 is accommodated in the lumen 922 of the catheter 920 in a state where the stent collecting tool 970 is contracted. A catching portion 971 formed at the distal end of the stent collecting tool 970 is formed from a shape memory alloy which is pre-formed so that the catching portion 971 can be expanded and deformed to be greater than the exterior dimension of the holding portion 720.

As illustrated, the stent collecting tool 970 is guided to the vicinity of the holding portion 720 via the channel 911 of the endoscope 910 and the catheter 920.

Figure 29:
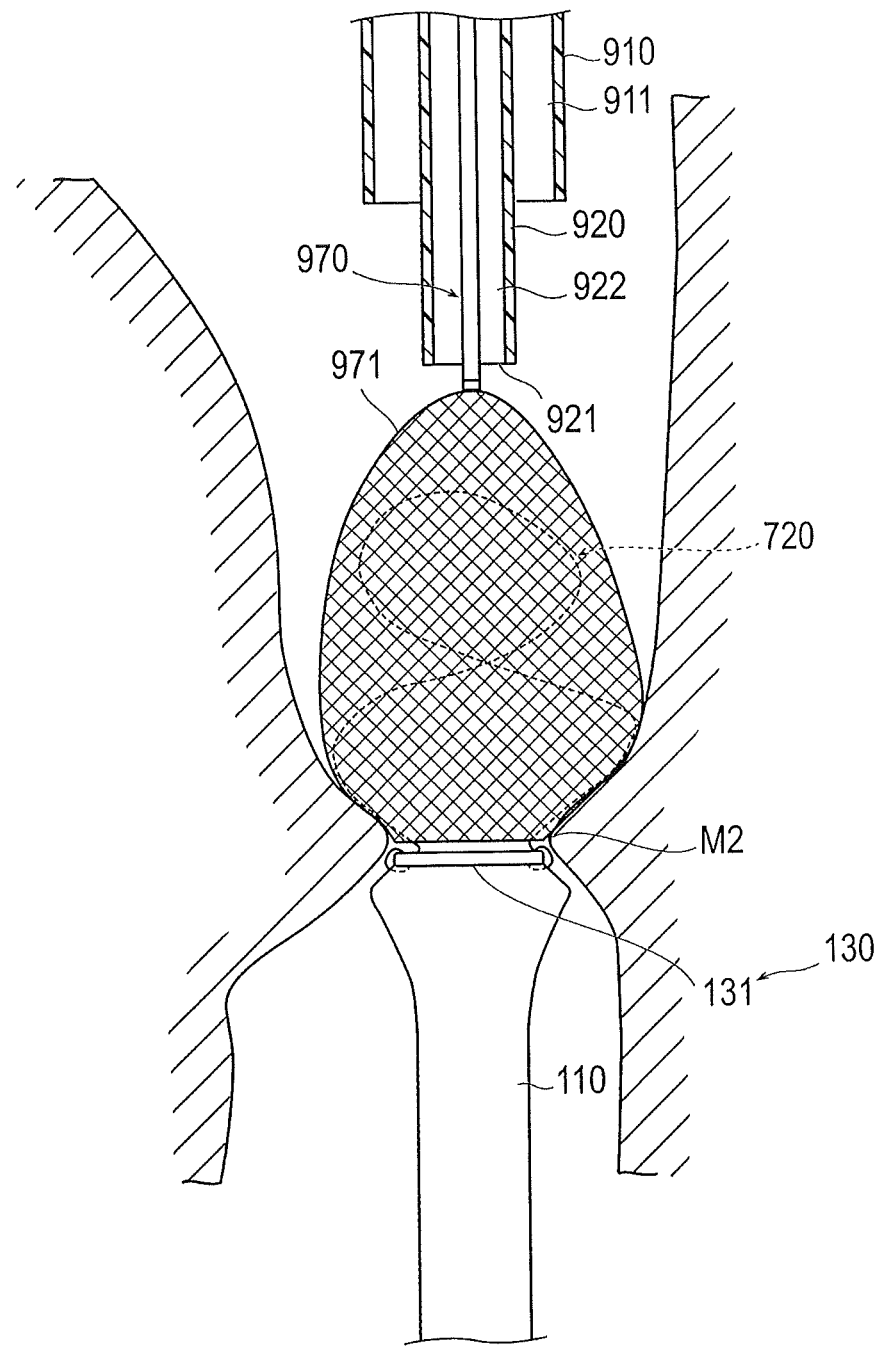
FIG. 29 is a cross-sectional view illustrating the sequence of removing the digestive tract device in the third embodiment from the living body.

Subsequently, as illustrated in FIG. 29, the operator protrudes the catching portion 971 of the stent collecting tool 970 from the distal end opening 921 of the catheter 920 (i.e., positions the catching portion 971 of the stent collecting tool 970 distally beyond the distal end opening 921 of the catheter 920). The catching portion 971 protruding from the catheter 920 is self-expanded, and is deformed to cover the entirety of the holding portion 720. The catching portion 971 is hollow so that the holding portion 720 is located inside the catching portion 971 when the catching portion 971 is expanded.

Figure 30:
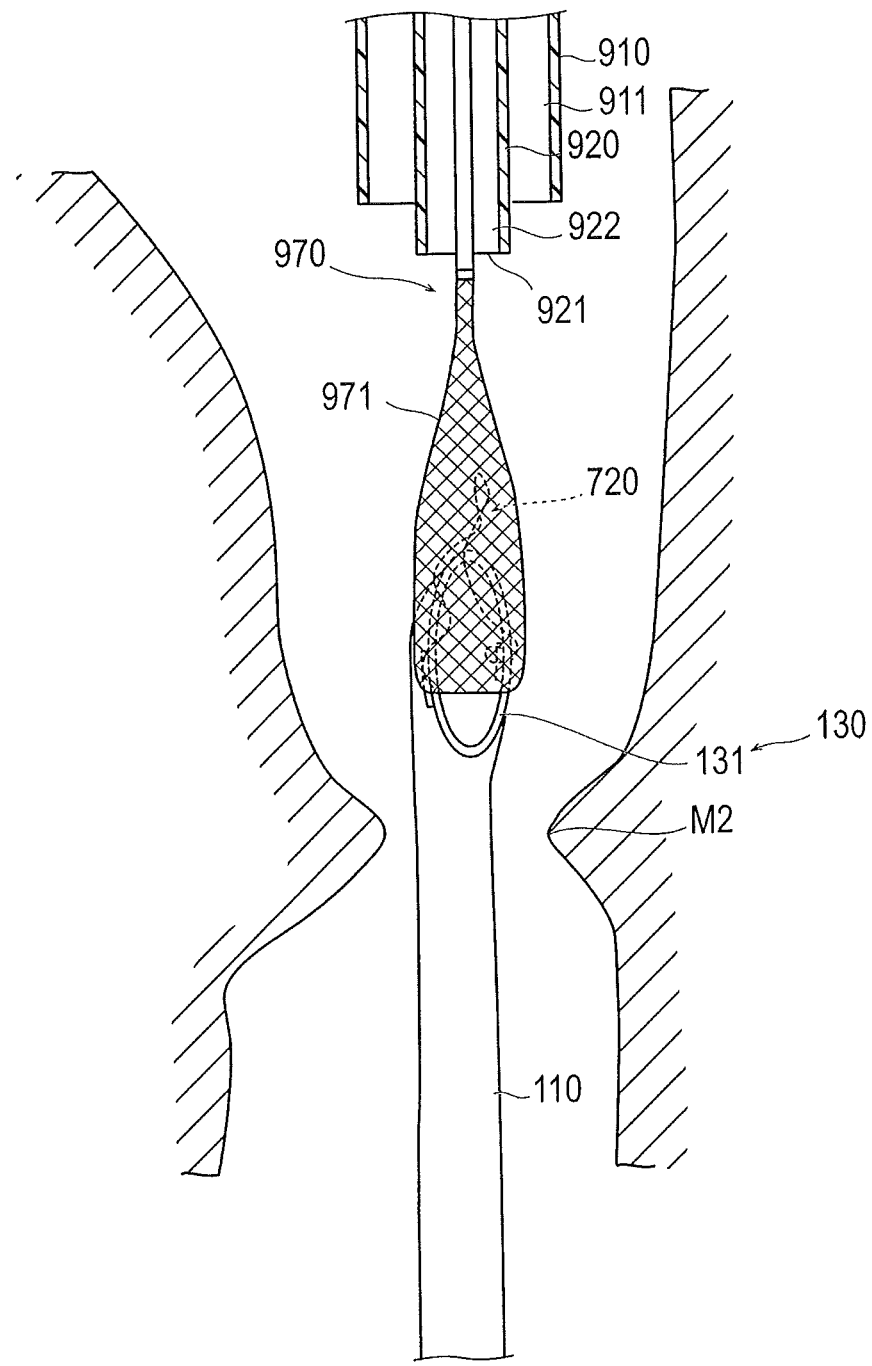
FIG. 30 is a cross-sectional view illustrating the sequence of removing the digestive tract device in the third embodiment from the living body.

Subsequently, as illustrated in FIG. 30, the operator contracts the catching portion 971 of the stent to the size such that the stent collecting tool 970 and the digestive tract device can be accommodated in the catheter 920. The operation of contracting the catching portion 971 of the stent collecting tool 970 can be performed using another member that can grip, for example, and contract the catching portion 971. For example, a tightening string or the like is provided on the stent collecting tool 970 in advance, and the operator can contract the catching portion 971 by pulling the string or the like via an operation by the hands.

After the catching portion 971 of the stent collecting tool 970, and the holding portion 720 are sufficiently contracted, the stent collecting tool 970 and the holding portion 720 are accommodated in the lumen 922 of the catheter 920. Thereafter, the operator ends the operation by removing the catheter 920 and the endoscope 910 from the digestive organ.

Also when the twisted portion 728 is formed in the holding portion 720, according to the aforementioned sequences, it is possible to indwell the digestive tract device in the digestive organ of the living body, and to remove the digestive tract device from the digestive organ of the living body in a simple and smooth manner. It is possible to remove the digestive tract device 100 by introducing a guide wire which is well known in the medical field into the endoscope 910 along with the catheter 920, and using the guide wire and the catheter 920. In addition, it is possible to remove the digestive tract device 100 by operating the guide wire and the catheter 920 under X-ray illumination without the aid of the endoscope 910.

Fourth Embodiment

Hereinafter, a digestive tract device in a fourth embodiment will be described. The same reference signs will be assigned to the same members as those in the first to third embodiments, and descriptions thereof will be omitted.

Figure 31:
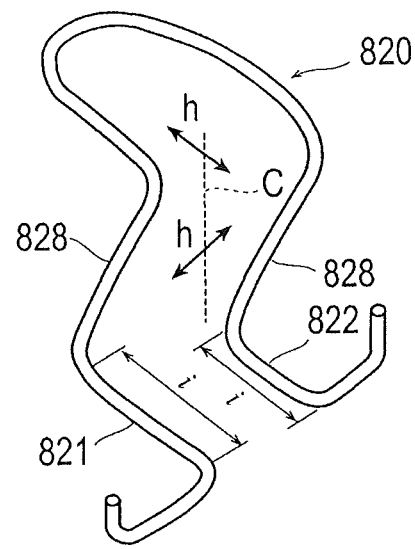
FIG. 31 is a perspective view illustrating a holding portion of a digestive tract device in a fourth embodiment.

As illustrated in FIG. 31, a holding portion of the digestive tract device in this embodiment includes a curved portion that is formed by bending a wire-shaped body in a direction intersecting an axis along the longitudinal direction of the tubular portion. In this regard, the digestive tract device in this embodiment is different from the digestive tract devices in the aforementioned embodiments.

A holding portion 820 includes curved portions 828 which are formed by bending a wire-shaped body (which forms the holding portion 820) multiple times in the direction (illustrated by arrow h in FIG. 31) intersecting the axis (the reference axis c) along the longitudinal direction of the tubular portion 110. Neck portions 821 and 822 serving as support portions are formed at predetermined positions on the proximal end side of the holding portion 820.

When the curved portions 828 are formed in the holding portion 820 as in this embodiment, friction between the neck portions 821 and 822 and the inner wall of the digestive organ is small, and thus the neck portions 821 and 822 can rather easily move in the longitudinal direction of the tubular portion 110 when an external force is applied to the holding portion 820. The holding portion 820 can move in the ranges (illustrated in FIG. 31) of the longitudinal lengths corresponding to the neck portions 821 and 822 of the holding portion 820. That is, the holding portion 820 can move within the range of these lengths in the longitudinal direction of the tubular portion 110 even if a smaller force is applied. Accordingly, it is possible to more suitably prevent a burden from being locally applied to a specific site on the pyloric ring M2 while the digestive tract device is indwelled.

The formation position of the curved portions 828 and the number of bending cycles (the number of bending cycles in the direction intersecting the reference axis c) of the wire-like body required to form the curved portions 828 are not limited to a specific position and a specific number of bending cycles insofar as the holding portion 820 can relatively easily move as described above.

Modification Example

Figure 32:
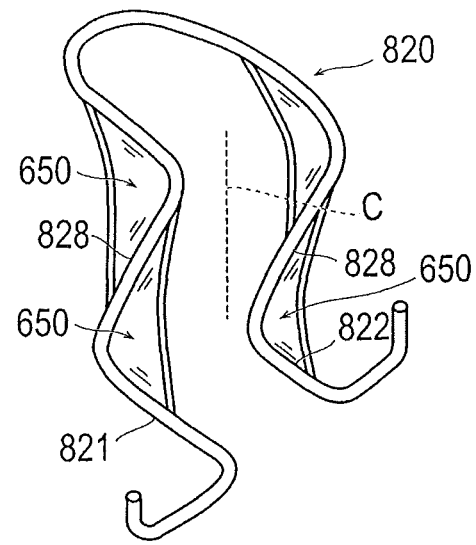
FIG. 32 is a perspective view illustrating a modification example of the holding portion of the digestive tract device in the fourth embodiment.

Hereinafter, a modification example of the digestive tract device in the fourth embodiment will be described. Features in this modification example that are the same as in the fourth embodiment are identified by common reference numerals and a detailed description of such features is not repeated As illustrated in FIG. 32, the movable blades 650 described in the second embodiment can be installed on the holding portion 820 of the digestive tract device in the fourth embodiment. Since the movable blades 650 are installed, the movable blades 650 and the curved portions 828 of the holding portion 820 cause the holding portion 820 to be able to move even if a smaller force is applied. For this reason, it is possible to suitably prevent a burden from being locally applied to a specific site on the pyloric ring M2 while the digestive tract device is indwelled.

For example, two sets of the movable blades 650 can be installed on each of the curved portions 828 of the holding portion 820. As illustrated, since the movable blades 650 are disposed at right and left positions, and at upper and lower positions with respect to the reference axis c, an external force can be uniformly applied to the movable blades 650. As a result, the holding portion 820 is caused to able to move even if a smaller force is applied.

In the description of the digestive tract device in the fourth embodiment illustrated in FIGS. 31 and 32, the curved portions 828 are formed in the holding portion 820 with the shape of Ω; however, a holding portion with any one of the shapes described in the modification examples of the first embodiment can be used as the holding portion 820. The number, the positions and the like of the movable blades 650 being installed are not limited to a specific number and specific positions. The tubular portion 110 is not illustrated in FIGS. 31 and 32; however, similar to the digestive tract device in the first embodiment, the tubular portion 110 can be engaged with the holding portion 820 via various engaging portions described in the first embodiment, or without the aid of the engaging portions.

The inventive digestive tract device disclosed here has been described in a plurality of the embodiments, and a plurality of the modification examples; however, aspects of the digestive tract device can be appropriately changed. For example, in each of the embodiments, the holding portion is formed from a wire or wire-shaped body; however, the holding portion can be changed insofar as the holding portion can be movably supported by the digestive organ via the support portions of the holding portion, and the holding portion can be formed from members other than a wire-like body. In addition, the support portions of the holding portion are in contact with the digestive organ of the living body at two points; however, contact is preferably made at two or more points, and it is possible to increase the number of contact points.

The indwelling method and the removal method described in the first and third embodiments can be applied to the digestive tract device in the embodiments and the modification examples. In the embodiments and the modification examples in which the movable blades are installed on the holding portion, when the indwelling method using a balloon catheter is adopted, the movable blades can interfere with a balloon. As a result, the indwelling method described in the first embodiment is preferably adopted when the movable blades are provided on the holding portion.

The detailed description above describes embodiments and modification examples of the digestive tract device representing examples of the inventive digestive tract device disclosed here. The invention is not limited, however, to the precise embodiments and variations described. Various changes, modifications and equivalents can effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A digestive tract device comprising:
a tubular portion that includes a through hole;
an annular member configured to hold a proximal portion of the tubular portion;
a holding portion extending proximally from the annular member, the holding portion being formed from a wire-shaped body; and
support portions provided in the holding portion, the support portions being configured to contact a plurality of sites of the digestive organ of the living body to support the holding portion; and
end portions provided in the support portions, the holding portion can being able to move in at least a circumferential direction of the annular member by the end portions passing through the annular member.

2. The digestive tract device according to claim 1, wherein the holding portion possesses a hourglass-shaped neck portion of the wire shaped body configured so that the neck portion contacts the digestive organ.

3. The digestive tract device according to claim 2, wherein the holding portion includes a twisted portion in which the wire-shaped body is twisted around an axis along the longitudinal direction of the tubular portion.

4. The digestive tract device according to claim 2, wherein the holding portion includes a curved portion formed by bending the wire-shaped body in a direction intersecting an axis along the longitudinal direction of the tubular portion.

5. The digestive tract device according to claim 4, wherein the holding portion has a movable blade configured to cause the holding portion to move when an external force is applied to the movable blade.

6. The digestive tract device according to claim 1, wherein the holding portion has a movable blade configured to cause the holding portion to move when an external force is applied to the movable blade.

7. The digestive tract device according to claim 1, further comprising: an engaging portion through which the holding portion is engaged with the tubular portion in such a way that the holding portion is rotatable relative to the tubular portion.

8. The digestive tract device according to claim 1, wherein the end portions extend in different directions.

9. The digestive tract device according to claim 1, wherein the support portions are provided at a distal side of the holding portion.

10. The digestive tract device according to claim 1, wherein a longitudinal axis of the holding portion coincides with a longitudinal axis of the tubular portion.

11. The digestive tract device according to claim 1, wherein the annular ring is configured to be disposed under a pyloric ring of the digestive organ.

12. The digestive tract device according to claim 1, wherein at least two twisted sections are provided in the wire-shaped body.

13. A method comprising:
   introducing a tubular portion and a holding portion into a digestive tract of a living body, the tubular portion possessing a length and including a through hole extending throughout the length of the tubular portion, and the holding portion holding the tubular portion on a proximal end of the tubular portion, the holding portion comprising a wire-shaped body;
   positioning the tubular portion and the holding portion in the digestive tract so that at least a part of the tubular portion is on a distal side of a site in the digestive tract of the living body, the site possessing an inner diameter smaller than an inner diameter of a portion of the digestive tract immediately proximal of the site and smaller than an inner diameter of a portion of the digestive tract immediately distal of the site;
   supporting the tubular portion in the digestive tract through contact of the holding portion with the digestive tract at a plurality of spaced apart locations on a proximal side of the site; and
   the holding portion in contact with the digestive tract being movable, relative to the tubular portion, in at least one of a circumferential direction of the tubular portion and a longitudinal direction of the tubular portion.

14. The method according to claim 13, wherein an annular member is attached to a proximal end of the tubular portion, and wherein the holding portion is wrapped around the annular member at two spaced apart locations on the annular member, the method further comprising rotating the wire-shaped body relative to the annular member and relative to the tubular portion.

15. The method according to claim 13, further comprising removing the tubular portion from the digestive tract by grasping the wire-shaped body through use of a removing tool and moving the removing tool together with the wire-shaped body and the tubular portion in a direction away from the site.

16. The method according to claim 13 wherein the holding portion includes movable blades, the method further comprising fluid flowing into the tubular portion causing application of a force to the movable blades resulting in circumferential movement of the holding portion relative to the tubular portion.

17. The method according to claim 13, wherein an annular member is attached to a proximal portion of the tubular portion, the holding portion including opposite hook-shaped engaging portions that engage the annular member so that the holding portion is rotatable relative to the engaging portion and the tubular portion.

18. The method according to claim 13, wherein the holding portion holds the tubular portion by way of an engaging portion, the engaging portion including a tubular portion-side annular member attached to the tubular portion, and a holding portion-side annular member attached to the holding portion, the holding portion-side annular member being engaged with the tubular portion-side annular member, the method further comprising rotating the holding portion and the holding portion-side annular member relative to the tubular portion and the tubular portion-side annular member.

19. The method according to claim 13, wherein the positioning of the tubular portion and the holding portion in the digestive tract includes positioning the tubular portion and the holding portion in the digestive tract while the holding portion is disposed on an expandable balloon, the method further comprising expanding the holding portion to contact the holding portion with the digestive tract at the plurality of spaced apart locations by expanding the balloon.

20. The method according to claim 13, further comprising removing the holding portion and the tubular portion from the digestive tract by bringing a catching portion into engagement with the holding portion and contracting the catching portion to also contract the holding portion, and moving the contracted catching portion and the contracted holding portion away from the site.

\* \* \* \* \*